United States Patent
Brown et al.

(10) Patent No.: US 7,479,368 B2
(45) Date of Patent: Jan. 20, 2009

(54) METHOD FOR DETECTING SUBJECTS HAVING PAGET'S DISEASE OF BONE

(75) Inventors: Jacques Brown, Cap-Rouge (CA); Vincent Raymond, Sainte-Foy (CA); Jean Morissette, Sainte-Foy (CA); Nancy Laurin, Val Belair (CA)

(73) Assignee: G.R.M.O. (Groupe de Recherche en Maladies Osseuses) Inc., Sainte-Foy, Québec (CA)

( * ) Notice: Subject to any disclaimer, the term of this patent is extended or adjusted under 35 U.S.C. 154(b) by 491 days.

(21) Appl. No.: 10/484,805

(22) PCT Filed: Jul. 30, 2002

(86) PCT No.: PCT/CA02/01186

§ 371 (c)(1),
(2), (4) Date: Sep. 20, 2004

(87) PCT Pub. No.: WO03/012134

PCT Pub. Date: Feb. 13, 2003

(65) Prior Publication Data

US 2005/0042611 A1    Feb. 24, 2005

Related U.S. Application Data

(60) Provisional application No. 60/308,135, filed on Jul. 30, 2001.

(51) Int. Cl.
    *C12Q 1/68*     (2006.01)
    *C07H 21/02*     (2006.01)
    *C07H 21/04*     (2006.01)

(52) U.S. Cl. .......................... 435/6; 536/23.1; 536/23.5

(58) Field of Classification Search ....................... None
See application file for complete search history.

(56) References Cited

U.S. PATENT DOCUMENTS 6,544,948 B1 *   4/2003   Schweighoffer et al. ...... 514/12

FOREIGN PATENT DOCUMENTS

| WO | WO 92/20794 | 11/1992 |
|---|---|---|
| WO | WO 96/38556 | 12/1996 |
| WO | WO 97/22255 | 6/1997 |

OTHER PUBLICATIONS

Cavey et al. Calcified Tissue International. 2006. 78: 271-277.*
Beyens et al. Calcified Tissue International. 2006. 79: 281-288.*
Joung I. et al., *Proc. Natl. Acad. Sci, USA*, 1996, vol. 93, No. 12, p. 5991-5995.
Laurin N. et al., *Am. J. Hum. Genet.*, 2002, vol. 70, No. 6, p. 1582-1588.
Hocking L.J. et al., *Human Molecular Genetics*, 2002, vol. 11, No. 22, p. 2735-2739.

* cited by examiner

*Primary Examiner*—Carla Myers
(74) *Attorney, Agent, or Firm*—France Côté; Bereskin & Parr

(57) ABSTRACT

Mutations in the atypical protein kinase C-interacting protein p62/sequestosome 1 (p62/SQSTM1) causing Paget disease of bone are described. Methods of detecting and treating Paget disease of bone are also disclosed.

2 Claims, 8 Drawing Sheets

FIGURE 3

Nucleic and protein sequences of the mutant (P392L) Sequestosome 1 (SQSTM1)/p62 gene

```
SQSTM1/P62:    1  ggcctgggtggcgaattcggcacgag

SQSTM1/P62:   27  gctcgccgctcgctatggcgtcgctcaccgtgaaggcctaccttctgggcaaggaggacg   86
Protein        1                  M  A  S  L  T  V  K  A  Y  L  L  G  K  E  D SQSTM1/P62:   87  cggcgcgcgagattcgccgcttcagcttctgctgcagccccgagcctgaggcggaagccg  146
Protein       16  A  A  R  E  I  R  R  F  S  F  C  C  S  P  E  P  E  A  E  A SQSTM1/P62:  147  aggctgcggcgggtccgggaccctgcgagcggctgctgagccgggtggccgccctgttcc  206
Protein       36  E  A  A  A  G  P  G  P  C  E  R  L  L  S  R  V  A  A  L  F SQSTM1/P62:  207  ccgcgctgcggcctggcggcttccaggcgcactaccgcgatgaggacggggacttggttg  266
Protein       56  P  A  L  R  P  G  G  F  Q  A  H  Y  R  D  E  D  G  D  L  V SQSTM1/P62:  267  ccttttccagtgacgaggaattgacaatggccatgtcctacgtgaaggatgacatcttcc  326
Protein       76  A  F  S  S  D  E  E  L  T  M  A  M  S  Y  V  K  D  D  I  F SQSTM1/P62:  327  gaatctacattaaagagaaaaaagagtgccggcgggaccaccgcccaccgtgtgctcagg  386
Protein       96  R  I  Y  I  K  E  K  K  E  C  R  R  D  H  R  P  P  C  A  Q SQSTM1/P62:  387  aggcgccccgcaacatggtgcaccccaatgtgatctgcgatggctgcaatgggcctgtgg  446
Protein      116  E  A  P  R  N  M  V  H  P  N  V  I  C  D  G  C  N  G  P  V SQSTM1/P62:  447  taggaacccgctacaagtgcagcgtctgcccagactacgacttgtgtagcgtctgcgagg  506
Protein      136  V  G  T  R  Y  K  C  S  V  C  P  D  Y  D  L  C  S  V  C  E SQSTM1/P62:  507  gaaagggcttgcaccggggggcacaccaagctcgcattccccagccccttcgggcacctgt  566
Protein      156  G  K  G  L  H  R  G  H  T  K  L  A  F  P  S  P  F  G  H  L SQSTM1/P62:  567  ctgagggcttctcgcacagccgctggctccggaaggtgaaacacggacacttcgggtggc  626
Protein      176  S  E  G  F  S  H  S  R  W  L  R  K  V  K  H  G  H  F  G  W SQSTM1/P62:  627  caggatgggaaatgggtccaccaggaaactggagcccacgtcctcctcgtgcaggggagg  686
Protein      196  P  G  W  E  M  G  P  P  G  N  W  S  P  R  P  P  R  A  G  E SQSTM1/P62:  687  cccgccctggccccacggcagaatcagcttctggtccatcggaggatccgagtgtgaatt  746
Protein      216  A  R  P  G  P  T  A  E  S  A  S  G  P  S  E  D  P  S  V  N SQSTM1/P62:  747  tcctgaagaacgttggggagagtgtggcagctgcccttagccctctgggcattgaagttg  806
Protein      236  F  L  K  N  V  G  E  S  V  A  A  A  L  S  P  L  G  I  E  V SQSTM1/P62:  807  atatcgatgtggagcacggagggaaaagaagccgcctgacccccgtctctccagagagtt  866
Protein      256  D  I  D  V  E  H  G  G  K  R  S  R  L  T  P  V  S  P  E  S SQSTM1/P62:  867  ccagcacagaggagaagagcagctcacagccaagcagctgctgctctgatcccagcaagc  926
Protein      276  S  S  T  E  E  K  S  S  S  Q  P  S  S  C  C  S  D  P  S  K SQSTM1/P62:  927  cggggtgggaatgttgagggcgccacgcagtctctggcggagcagatgagaaagatcgcct  986
Protein      296  P  G  G  N  V  E  G  A  T  Q  S  L  A  E  Q  M  R  K  I  A SQSTM1/P62:  987  tggagtccgaggggcgccctgaggaacagatggagtcggataactgttcaggaggagatg 1046
Protein      316  L  E  S  E  G  R  P  E  E  Q  M  E  S  D  N  C  S  G  G  D SQSTM1/P62: 1047  atgactggacccatctgtcttcaaaagaagtggacccgtctacaggtgaactccagtccc 1106
Protein      336  D  D  W  T  H  L  S  S  K  E  V  D  P  S  T  G  E  L  Q  S SQSTM1/P62: 1107  tacagatgccagaatccgaagggccaagctctctggacccctcccaggagggacccacag 1166
Protein      356  L  Q  M  P  E  S  E  G  P  S  S  L  D  P  S  Q  E  G  P  T SQSTM1/P62: 1167  ggctgaaggaagctgccttgtacccacatctcccgccagaggctgacctgcggctgattg 1226
Protein      376  G  L  K  E  A  A  L  Y  P  H  L  P  P  E  A  D  L  R  L  I SQSTM1/P62: 1227  agtccctctcccagatgctgtccatgggcttctctgatgaaggcggctggctcaccaggc 1286
Protein      396  E  S  L  S  Q  M  L  S  M  G  F  S  D  E  G  G  W  L  T  R SQSTM1/P62: 1287  tcctgcagaccaagaactatgacatcggagcggctctggacaccatccagtattcaaagc 1346
protein      416  L  L  Q  T  K  N  Y  D  I  G  A  A  L  D  T  I  Q  Y  S  K SQSTM1/P62: 1347  atccccccgccgttgtgaccacttttgcccacctcttctgcgtgcccctcttctgtctcat 1406
Protein      436  H  P  P  P  L  STOP SQSTM1/P62: 1407  agttgtgttaagcttgcgtagaattgcaggtctctgtacaggccagtttctctgccttct 1466
```

FIGURE 3 (cont'd)

```
SQSTM1/P62:  1467  tccaggatcaggggttagggtgcaagaagccatttagggcagcaaaacaagtgacatgaa  1526
SQSTM1/P62:  1527  gggagggtccctgtgtgtgtgtgtgtgctgatgtttcctgggtgccctggctccttgcag  1586
SQSTM1/P62:  1587  cagggctgggcctgcgagacccaaggctcactgcagcgcgctcctgaccctccctgcag  1646
SQSTM1/P62:  1647  gggctacgttagcagcccagcacatagcttgcctaatggctttcactttctcttttgttt  1706
SQSTM1/P62:  1707  taaatgactcataggtccctgacatttagttgattattttctgctacagacctggtacac  1766
SQSTM1/P62:  1767  tctgattttagataaagtaagcctaggtgttgtcagcaggcaggctggggaggccagtgt  1826
SQSTM1/P62:  1827  tgtgggcttcctgctgggactgagaaggctcacgaagggcatccgcaatgttggtttcac  1886
SQSTM1/P62:  1887  tgagagctgcctcctggtctcttcaccactgtagttctctcatttccaaaccatcagctg  1946
SQSTM1/P62:  1947  cttttaaaataagatctctttgtagccatcctgttaaatttgtaaacaatctaattaaat  2006
SQSTM1/P62:  2007  ggcatcagcactttaaccaatgacgtttgcatagagagaaatgattgacagtaagtttat  2066
SQSTM1/P62:  2067  tgttaatggttcttacagagtatctttaaaagtgccttaggggaaccctgtccctcctaa  2126
SQSTM1/P62:  2127  caagtgtatctcgattaataacctgccagtcccagatcacacatcatcatcgaagtcttc  2186
SQSTM1/P62:  2187  cccagttataaagaggtcacatagtcgtgtgggtcgaggattctgtgcctccaggaccag  2246
SQSTM1/P62:  2247  gggcccaccctctgcccagggagtccttgcgtcccatgaggtcttcccgcaaggcctctc  2306
SQSTM1/P62:  2307  agacccagatgtgacggggtgtgtggcccgaggaagctggacagcggcagtgggcctgct  2366
SQSTM1/P62:  2367  gaggccttctcttgaggcctgtgctctgggggtcccttgcttagcctgtgctggaccagc  2426
SQSTM1/P62:  2427  tggcctggggtccctctgaagagaccttggctgctcactgtccacatgtgaacttttct  2486
SQSTM1/P62:  2487  aggtggcaggacaaatcgcgcccatttagaggatgtggctgtaacctgctggatgggact  2546
SQSTM1/P62:  2547  ccatagctccttcccaggacccctcagctccccggcactgcagtctgcagagttctcctg  2606
SQSTM1/P62:  2607  gaggcagggctgctgccttgtttccacttccatgtcaggccagcctgtccctgaaagag  2666
SQSTM1/P62:  2667  aagatggccatgccctccatttgtaagaacaatgccagggcccaggaggaccgcctgccc  2726
SQSTM1/P62:  2727  tgcctgggccttggctgggcctctggttctgacactttctgctggaagctgtcaggctgg  2786
SQSTM1/P62:  2787  gacaggctttgattttgagggttagcaagacaaagcaaataaatgccttccacctcaccg  2846
SQSTM1/P62:  2847  caaaaaaaaaaaaaaaaaaaaaaaa  2870
```

FIGURE 4

EXON 1 gaggggggccg ggagacctng agcgaggggt agc<u>gggaaag gggagagtag tga</u>aggggcc
                          → tctgcagggc ggctctcgcg ccgcgacgac gtggcggggg cggggagggc gcgagagact ccgcccctct cgaggcgggg cggggcctcc gcgttcgcta caaaagccGC GCGGCGGCTG

CGACCGGGAC CGGCGGCTTT CCGCGAGCTG GCCGCTGGCT ATGCCGTCGC TCAGCGTGAA

GGCCTACCTT CTGCGCAAGG AGGACGCGGC GCGCGAGATT CCCCGCTTCA GCTTCTGCTG

CAGCCCCGAG GCTGAGGCGG AAGGCGAGGC TGCGCCGGGT CCGGGACGGT GCGAGGGCGT

GCTGAGCGGG GTGGCCGGCC TGTTCGGCCG GCTGCGGCCT GGCGGCTTCC AGGCGCACTA

CCGCGgtgag cgggccgggg agcggcgggg gcggtgacgc aggccggaca cggcctcctg ccgcggggtg gctgccccct cccttctcgg cgacgcctgg cgggccgtga gggggtctgc gctggctgct ccctggatgg cggtggcctg catgggtccc cagttcggcc atgggagccg gcctgg<u>tgac tggagtggtg accaag</u>gccg ggacccgctg ctcagcgtcg gccccctggg
    ←

EXON 2 aggtcggagc actcaccttc caggaggtgc cagagca<u>agg gggtagtctt gcctctc</u>act
                          → cctgccctct gtggctcaag taggtgtgtt tgtttatagc cctgtgagtg tccctttcat acttgcctca gcccattcca gcagcttatg tccagctgag aaccctggg tgctcacgtg ctgtcttta aacaatctag ATGAGGACGG GGACTTGGTT GCCTTTTCGA GTGACGACGA ATTGACAATG GCCATGTCCT ACGTGAAGGA TGACATCTTC CGAATCTACA TTAAAGgtaa ggggctgctc tggggctgc ctgaagccag ctcagcttgt actcagttcc ctgctgagta aaaaacaggg ctcgatgttc caccaatgaa ggg<u>gtcagca atttgagggc tgt</u>ttaagac
                          ←

FIGURE 4 (cont'd)

EXONS 3 et 4 agtgacagcc ccacagtgac gacagagggg gaggacttta ggggtccca ccctagcggc
→
tctctttacc cttcctgtag AGAAAAAAGA GTGCGGGCGG GACCACCGGC CACCGTGTGG
TCAGGAGCCG CCCCGCAACA TGGTGCAGCC CAATGTGATC TGCGATGGCT GCAATGGGCC
TGTGGTAGGA ACCCGCTACA AGTGCAGCGT CTGCCCAGAC TACGACTTGT GTAGCGTCTG
CGAGGGAAAG GGGTTGCACC GGGGGCACAC GAAGCTCGCA TTCCCCAGCC CCTTCGGGA
CCTCTCTGAG gtgagcaggc cctctgtgca ggcctggggt gggctcaggg tggcaggaac
→
cttgacccgc tcactgcctg ccgctctgct aattcctccc ccagGGCTTC TGCCACAGCC
GCTGGCTCCG GAAGGTGAAA CACGGACACT TCGGGTGGGC AGGATGGAA ATGGTCCAG
←
CAGGAAACTG GAGCCCACGT CCTCCTCGTC CAGGGAGGC CCGGCCTGGC CCCACGGCAG
AATCAGgtga ggcttgtgtt ggaacctgct tctgattggt gacagtagtc aggcagcctg
tgtgcagggc ccttgtgcaa agcgtgtgtg caaggcaaga attcaggata ccccccacct
←

EXON 5 ggtgcagagt gggaggaagg agaggggat gctgagtggg tcactggaca agatgtccgg
→
gttaaaggtc acccgggaac acagggacct tggcaagaag gtgacaggac tgtgacaggt
atccaaggca ttaaagatat ctttatctta tctttgtaaa aatcaaagCT TCTGGTCCAT
GGGAGGATCC GAGTGTGAAT TTCCTCAAGA AGGTTGGGA GAGTGTGGCA GCTGCCCTTA
GCCCTCTGGg tgagtgcacc tccttgccca gtgcttccct aactcagcct gcactttatg
taactttcac ctggaatact gcaaaggaat gggtaattga catgcccttg acactggtga
ggatttgttg cctcaaatca accttTagta gtgctggacc acgggcaact caaggttgaa
←

FIGURE 4 (cont'd)

EXON 6

```
acttagctgc ttgtggggac tgaacgttga gatcttcgtg agtctgtagt ctccacaggc
         →
caagctcctg cttgcaggtg catccttggg ggaacttcac ggcttgctct ttcctcctcc
gcctctagGC ATTGAAGTTG ATATCGATGT GGACCACGGA GGGAAAAGAA GCCGCCTGAC
CCGCGTCTGT CCAGAGAGTT CCAGGAGAGA GGAGAAGAGG AGCTGACAGC CAAGCAGCTG
CTGCTGTGAC GCCAGCAAGC CGGGTGGGAA TGTTGAGCGC GCCACCGAGT CTCTGGCGGA
GCAGATGAGG AAGATCGGCT TGGAGTCGGA GGGGCGGCCT GAGgcaagcc tgtgccctc
ccgccacctg ggaccacggc cagcctagtg atctgtggcc tgcacctccg cctcatcctc
agcacctctg cagcccact tacaaacccg agggagctgc tgctgctgca gtgatgtctg
                                                              ←
```

EXON 7

```
ggccactgtt cccctagac ccctgcagcc ttaactgcac gtgtgcatgc gtgctcccg
                                          →
actgtctgcc aggagccagg gccatggtca ggcttggcct gttgcgcgtg tctcctgtgt
gctcatggtg agttttgttc cagGAACAGA TGGAGTCGGA TAACTGTTCA GGAGGAGATG
ATGACTGGAC CCATCTGTCT TGAAAAGAAG TGGACCCGTC TACAGGTGAA GTCGAGTCCC
TACAGATGGC AGAATCCGAA GGGCCAAGGT CTCTGGACCG CTCCCAGGAG GGACCCACAG
GGCTGAAGGA AGGTGGCTTG TACCGACATC TGCCGCCAGg caagtgaacc aagaggtttt
gtacatattc ctacctttcc ctttagagca tcctgccctc ctctgatttc agcgacacaa
acagaaggat gagatgttct ccactgcagg gctgtctgta ggtgtgggag gttaggagtt
                                                              ←
ggttttgtcc tattatgtgt acctgagca atagcgagta agctctgcta atgcagttct
```

FIGURE 4 (cont'd)

EXON 8

```
ttggccctttt acagggaaag caggtccact gtggcctgtg aggacgagag ctctgggcag
                           ─────────────────────→
gctcggacac tggcagaccc tggtcctggc tggccaaggc agcagggtat gtgtttcggg tcactcacag ggctcagcac cactcctcat ggcttcctta ctgtttcggc agAGGCTGAC

CCGCGGCTGA TTGAGTCCCT CTCCCAGATG CTGTCCATGG GGTTCTCTGA TGAAGGCGGC

TGGCTCACCA GGCTCCTGCA GACCAAGAAC TATGACATCG CAGCGGCTGT GGAGAGCATC

CAGTATTCAA AGCATCCCCG GCGGTTCTGA CCACTTTTGC CCACCTCTTC TCCGTGCCCC

TCTTCTGTCT CATAGTTGTG TTAAGCTTGC GTAGAATTGC AGGTCTCTGT ACGGGCCAGT

TTCTCTGCCT TCTTCGAGGA TCAGCGGTTA GGGTCCAACA AGCCATTTAG GGCAGCAAAA

CAAGTGAGAT GAAGGCAGGG TCCCTGTGTG TGTGTGTCCT GATGTTTCCT GGGTGCCCTG

GCTCCTTGCA GCAGGGCTGG GCCTGCGACA CCGAAGGCTG ACTGCAGCGC GCTCCTGACC
                                   ←─────────────────
CCTCCCTGCA GGGGCTAGGT TAGCAGCCCA GCACATAGGT TGCCTAATGG CTTTCACTTT

CTCTTTTGTT TTAAATCACT CATAGCTCCC TGACATTTAG TTGATTATTT TCTGGTACAG

ACCTGGTACA CTCTGATTTT AGATAAAGTA AGCCTACGTG TTGTCAGCAG GCAGCCTGGG

GAGCCAGTG TTGTGGGCTT CCTGCTGGGA CTGAGAAGGC TGAGGAAGGG CATCCGCAAT

GTTGGTTTCA CTGAGAGCTG CCTCCTCGTC TCTTCACCAG TGTAGTTGTC TGATTTCCAA

ACCATGAGGT GCTTTTAAAA TAAGATGTCT TTGTAGCCAT GCTGTTAAAT TTGTAAACAA

TGTAATTAAA TGGCATGAGG ACTTTAACCA ATgacgtttg catagagaga aatgattgac agtaagttta ttgttaatgg ttcttacaga gtatctttaa aagtgcctta ggggaaccct
```

METHOD FOR DETECTING SUBJECTS HAVING PAGET'S DISEASE OF BONE

FIELD OF THE INVENTION

The present invention relates to methods and materials to detect a human gene located at the PDB3 locus on chromosome 5q35: the atypical protein kinase C-interacting protein p62/sequestosome 1 (p62/SQSTM1), some mutants of which cause Paget disease of bone. The invention also relates to therapeutic methods for treating Paget disease of bone.

BACKGROUND OF THE INVENTION

Paget disease of bone (Mendelian Inheritance in Man, MIM 167250) is a localized monostotic (only one site is affected) or polyostotic (several sites are affected) progressive metabolic bone disorder. The disease is characterized by an increased remodeling process in which abnormal bone resorption remains coupled to new osteoblastic bone formation. The process is initiated by increases in osteoclast-mediated bone resorption, with subsequent compensatory increases in new bone formation, resulting in a disorganized mosaic of woven and lamellar bone at affected sites. This structural change produces bone that is expanded in size, less compact, more vascular, and more susceptible to deformity or fracture than is normal (Siris and Canfield 1990).

Clinical signs and symptoms will vary from one patient to the next depending on the number and location of affected skeletal sites, as well as on the rapidity of the abnormal bone turnover. It is believed that most patients are asymptomatic, but about 5% of pagetic patients present symptoms requiring treatment (Kanis 1998). The most frequent complaints are bone pain, enlargement and deformities (Kanis 1998). Other manifestations of the disease include increased susceptibility to fractures, excessive warmth over bone from hypervascularity, deafness and neurological complications caused in most instances by compression of neural tissues adjacent to pagetic bone, as well as an increased susceptibility to osteosarcomas (Hamdy 1995).

Paget disease of bone usually appears after 40 years of age (Klein and Norman 1995) and mainly affects the axial skeleton. In Western countries, Paget disease of bone is the second most common metabolic bone disorder after osteoporosis. In the United States, the disorder has an estimated frequency of 1-3% in the population over age 40 and of 8-10% for those over age 80 (Siris and Canfield 1990).

The etiology of Paget disease of bone remains unknown. However, there is compelling evidence that genetic factors play a major role in the etiology of the disorder. The disease is most common in Western Europe (Detheridge et al. 1983), North America (Rosenbaum and Hanson 1969; Guyer and Chamberlain 1980), Australia (Barker 1984) and New Zealand (Reasbeck et al. 1983) with the highest prevalence in the United Kingdom, particularly in Lancashire (prevalence >6.3%) (Barker et al. 1980). Familial risk for Paget disease of bone has been evaluated by several authors. Sofaer et al. observed a tenfold increased prevalence among the parents and siblings of patients compared to their spouses (Sofaer et al. 1983). In the United States, Siris et al. further reported an affected first-degree relative in 12% of pagetic patients and calculated a seven-fold increased risk of developing the disease for first-degree relatives (Siris et al. 1991). In Spain, Mirales-Piga et al. observed that 40% of their index cases had at least one first-degree relative affected with Paget disease of bone (Morales-Piga et al. 1995). Familial clustering of Paget disease of bone was also frequently documented (Sofaer et al. 1983; Siris et al. 1991; Morales-Piga et al. 1995; Haslam et al. 1998; Hocking et al. 2000). In the kindreds investigated to date, Paget disease of bone appeared to be transmitted with an autosomal dominant mode of inheritance with incomplete penetrance.

Suggestive evidence for linkage was first reported between Paget disease of bone and the HLA locus at 6p (Fotino et al. 1977; Tilyard et al. 1982). This potential locus was named PDB1 (MIM 167250). However, further studies did not confirm linkage at this site (Breanndan Moore and Hoffman 1988; Nance et al. 2000; Good et al. 2001), suggesting that the role of the HLA locus may be of minor importance in the etiology of Paget disease of bone.

A rare bone disorder, familial expansile osteolysis [FEO (MIM #174810)], has been mapped to chromosome 18q21-q22 (Hughes et al. 1994). Using a candidate locus approach and a large pagetic family, Cody et al. reported evidence for linkage between Paget disease of bone and the same 18q region with a LOD score of 3.40 at D18S42 (Cody et al. 1997). This locus was called PDB2 (MIM 602080). These authors proposed that the gene(s) responsible for FEO and Paget disease of bone were either closely linked or were allelic variants of the same mutant gene. Subsequently, Haslam et al. confirmed linkage to 18q in five pagetic families and observed genetic heterogeneity in three other kindreds (Haslam et al. 1998). More recent studies confirmed genetic heterogeneity of the disorder and suggested that linkage of Paget at 18q21-q22 was relatively uncommon (Hocking et al. 2000; Nance et al. 2000; Good et al. 2001).

Recently, the FEO disease gene has been identified as the TNFRSF11A gene (MIM 603499) that encodes RANK, the receptor activator of nuclear factor-κB (Hughes et al. 2000). The same heterozygotic insertion (84dup18) was detected in TNFRSF11A exon 1 in three families with FEO or FEO-related cases. One pedigree of Japanese origin with atypical Paget disease of bone also carried a 27 bp insertion (75dup27) in the TNFRSF11A gene. Their uncommon symptoms included early onset and dental problems, suggesting that these patients may suffer from a milder form of FEO or a particular early-onset form of Paget disease of bone (Leach et al. 2001). No RANK mutations have yet been reported for patients manifesting typical cases of Paget disease of bone (Hughes et al. 2000; Sparks et al. 2001). These observations show that the gene(s) causing the typical form of Paget disease of bone still remains to be characterized.

SUMMARY OF THE INVENTION

The present invention relates to methods and materials used to isolate and detect a human gene located at the PDB3 locus causing Paget disease of bone. The gene encodes the atypical protein kinase C-interacting protein p62 which is also referred to as sequestosome 1 (SQSTM1), some alleles of which cause Paget disease of bone. More specifically, the present invention relates to germline mutations in the atypical protein kinase C-interacting protein/sequestosome 1 (p62/SQSTM1) and their use in the diagnosis and predisposition to Paget disease of bone. The invention also relates to presymptomatic therapy of individuals who carry deleterious alleles of the p62/SQSTM1 gene. The invention also relates to the therapy of Paget disease of bone of individuals who have mutations in the p62/SQSTM1 gene (including gene therapy, protein replacement therapy, protein mimetics and inhibitors, RNA interference and antisense). The invention also relates to presymptomatic therapy of individuals who carry deleterious alleles of the p62/SQSTM1 gene. The invention further relates to the screening of drugs for Paget disease of bone.

Finally, the invention relates to the screening of the p62/SQSTM1 gene for mutations, which are useful for diagnosing Paget disease of bone.

Accordingly, the present invention provides an isolated nucleic acid molecule comprising a sequence encoding an atypical protein kinase C interacting protein having a molecular weight of approximately 62 kD (p62/SQSTM1) that is diagnostic of a disease of the bone. In a preferred embodiment, the isolated nucleic acid molecule encodes a mutated p62/SQSTM1 protein that is diagnostic of Paget disease of bone.

In another embodiment, the invention provides an isolated atypical protein kinase C interacting protein having a molecular weight of approximately 62 kD (p62/SQSTM1) that is diagnostic of a disease of the bone. In a preferred embodiment, the protein is a mutated from of p62/SQSTM1 that is diagnostic of Paget disease of bone.

In a further embodiment, the invention provides for a method of identifying substances which can bind with a mutated p62/SQSTM1 protein, comprising the steps of:

(a) incubating a mutated p62/SQSTM1 protein and a test substrate, under conditions which allow for formation of a complex between the p62/SQSTM1 protein and the test substance, and (b) assaying for complexes of the mutated p62/SQSTM1 protein and a test substance, for free substance or for non complexed mutated p62/SQSTM1 protein, wherein the presence of complexes indicates that the test substance is capable of binding to the mutated p62/SQSTM1 protein.

The invention also provides for methods for identifying a compound that affects mutated p62/SQSTM1 protein activity or expression comprising:

(a) incubating a test compound with a mutated p62/SQSTM1 protein or a nucleic acid encoding a mutated p62/SQSTM1 protein; and (b) determining an amount of mutated p62/SQSTM1 protein activity or expression and comparing with a control, wherein a change in the mutated p62/SQSTM1 protein activity or expression as compared to the control indicates that the test compound has an effect on mutated p62/SQSTM1 protein activity or expression.

In another embodiment, the invention provides a method of detecting a condition associated with a mutated p62/SQSTM1 protein comprising assaying a sample for (a) a nucleic acid molecule encoding a mutated p62/SQSTM1 protein or a fragment thereof or (b) a mutated p62/SQSTM1 protein or a fragment thereof.

In a further embodiment, the invention provides a method of treating a bone disease comprising of administering to a cell or animal in need thereof, an effective amount of agent that modulates p62/SQSTM1 expression and/or activity. The invention also provides a use of an effective amount of an agent that modulates p62/SQSTM1 expression and/or activity to treat a bone. disease. In a preferred embodiment, the bone disease is Paget disease of bone.

In yet another embodiment, the invention provides for a non-human animal carrying a mutation in the gene encoding a p62/SQSTM1 protein corresponding to a human P392L residue wherein the animal is a model for bone disease.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

Certain embodiments of the invention are described, reference being made to the accompanying drawings, wherein:

FIG. 1 also shows the p62/SQSTM1 transcription unit showing the location of the exons of p62/SQSTM1 relative to a BAC contig that was constructed in silico. The individual exons are numbered, and these numbers correspond to the sequences shown in FIG. 4.

FIG. 3 is a diagram showing the nucleic and protein sequence of mutated p62/SQSTM1 as set forth in SEQ ID NO: 3 and SEQ ID NO: 4, respectively. The figure depicts the position for the mutation causing Paget disease of bone.

FIG. 4 is a diagram showing part of the genomic sequence of the p62/SQSTM1 gene SEQ ID NO: 37 including complete sequence of the eight exons as well as the sequences of the intron/exon boundaries. Sequences of the primers used for sequencing the exons are provided in Table 1 and 2. Table 1 shows the sequences of primers of microsatellite markers used to genotype in the p62/SQSTM1 gene to sequence the p62/SQSTM1 gene.

DETAILED DESCRIPTION OF THE INVENTION

Figure 1:
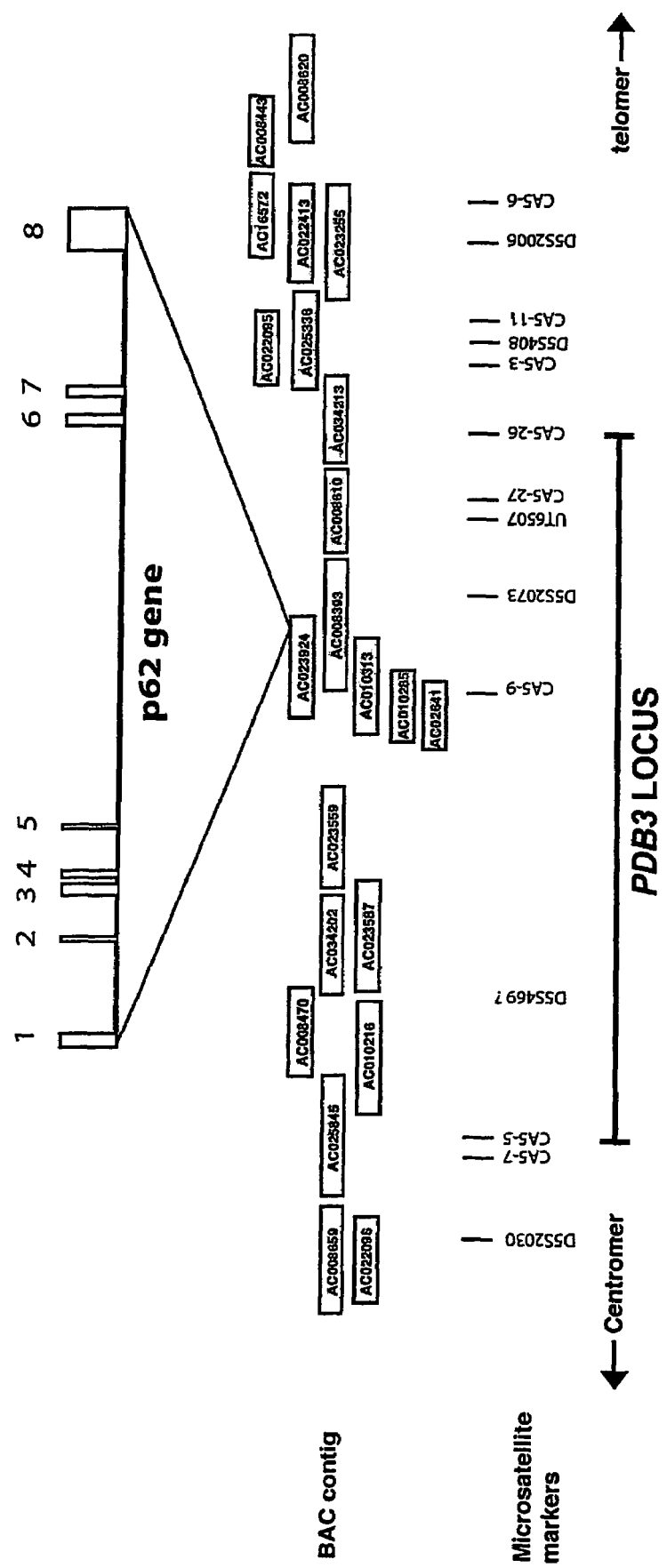
FIG. 1 is a diagram showing the order of genetic markers at the PDB3 locus neighboring the p62/SQSTM1 gene, a schematic map of BACs spanning the PDB3 locus, and also shows the location of the p62/SQSTM1 gene within the genetically defined interval.
Figure 2:
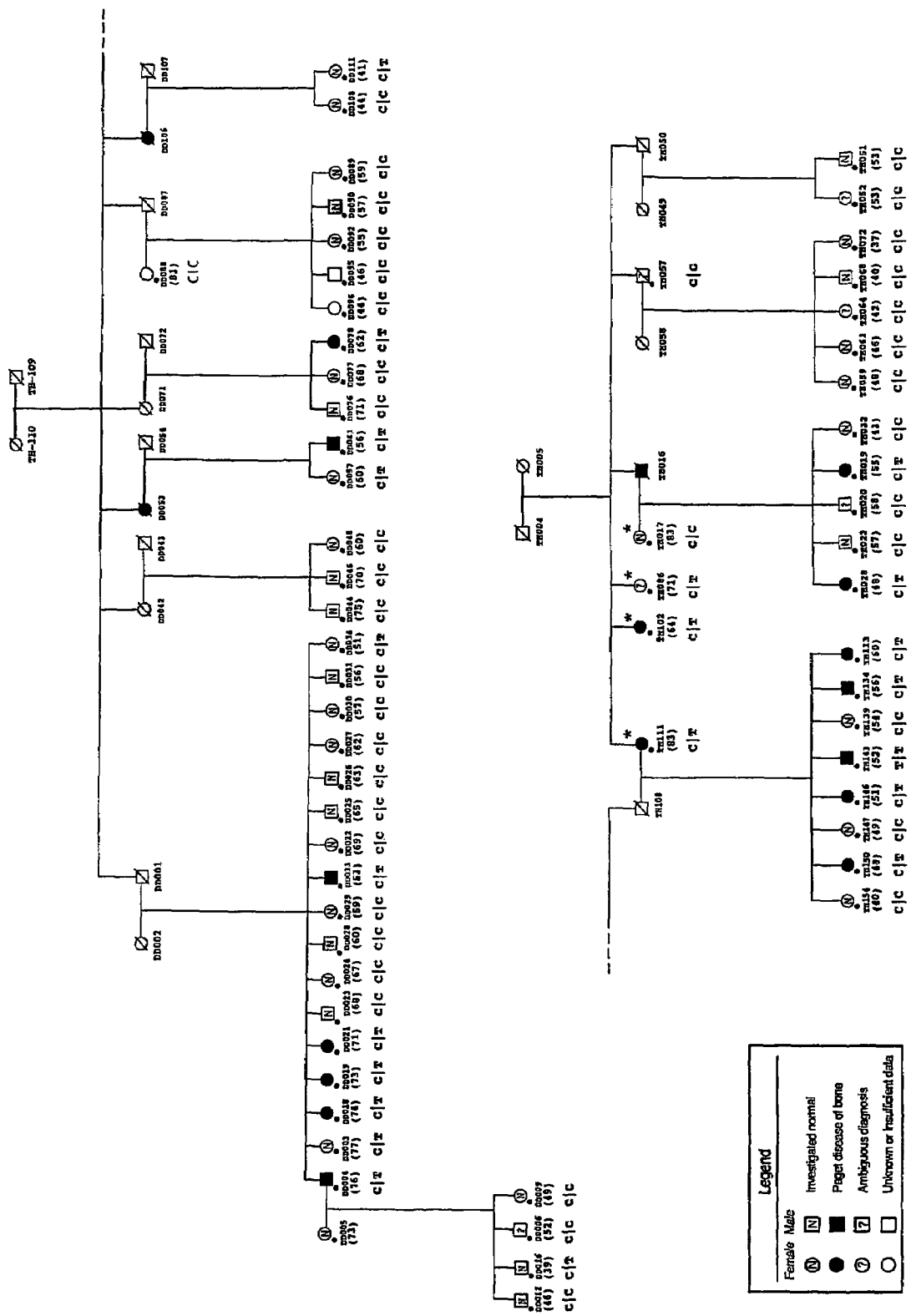
FIG. 2 is a diagram showing the segregation of the mutation changing amino acid Pro to Leu at amino acid position 392 in the p62/SQSTM1 protein coding sequence within one large family affected by Paget disease of bone.

The inventors performed genetic linkage analysis in 24 large French-Canadian families (479 individuals) in which Paget disease of bone was segregating as an autosomal dominant trait. After excluding PDB2, a genome-wide scan was performed on the three most informative family nuclei which included 44 individuals. LOD scores greater than 1.0 were observed at seven locations on the human genome. The 24 families were then used to detect strong evidence for linkage at chromosome 5q35-qter. Under heterogeneity, a maximum LOD score value of 8.58 was obtained at D5S2073 with θ=0.1. The same characteristic haplotype was carried by all patients in eight families, suggesting a founder effect. A recombination event in a key family confined the disease region within a 6 cM interval between D5S469 and the telomere. The 16 other families, with very low conditional probability of linkage at 5q35-qter, were further used to map a second locus at 5q31. Under heterogeneity, a maximum LOD score value of 3.70 was detected at D5S500 with θ=0.00. Recombination events refined the 5q31 region within 11.7 cM between D5S642 and D5S1972. These observations therefore demonstrated the mapping of two novel loci for Paget disease of bone and provide further evidence for its genetic heterogeneity. The 5q35-qter and 5q31 loci have been named PDB3 and PDB4, respectively.

The inventors further screened many genes at the PDB3 locus for their involvement in Paget disease of bone. Among the many genes that were screened for mutation, one of these genes was the atypical protein kinase C-interacting protein p62 (p62), also known as sequestosome 1 (SQSTM1). One nucleotide variation at nucleotide position 1215 of the p62/SQSTM1 gene, changing amino acid Pro to Leu at amino acid position 392 (Pro392Leu), was detected in 11 kindreds of the family resources. This nonconservative change flanks the ubiquitin-associated domain (UBA) (position 394-440) of the protein. This variation was found to be segregating with the disorder in these families. Sequencing the 112 sporadic cases revealed that 18 patients also carried the variation. Sequencing of 86 non-affected spouses and 205 individuals from the general population did not reveal any change in the wild-type p62/SQSTM1 sequence. These data therefore demonstrate that the C to T variation at position 1215 of the p62/SQSTM1 gene is, in fact, a mutation causing Paget disease of bone.

The p62/SQSTM1 gene was identified in 1995 (PNAS 92: 12338 (1995)). p62/SQSTM1 was originally described as a phosphoprotein of 62 kilodalton (kD) that was interacting with p56lck. The protein was shown to be located in the cytosol and to bind ubiquitin. p62/SQSTM1 interacts with several signal transduction molecules including the tyrosine kinase p56lck and the atypical protein kinase C-zeta. Recent experiments showed that p62/SQSTM1 acts as a point of convergence of the IL-1 and TNFalpha signaling pathways. Interaction between p62/SQSTM1 with RIP links the atypical protein kinases C to the activation of NF-kappa B (NFκB) by the TNFalpha signaling pathway. Indeed, recent evidences suggest that p62/SQSTM1 selectively interact with TRAF6 and RIP and is an important intermediary in interleukin-1 (IL-1) and tumor necrosis factor α (TNFα) signaling toward NFκB activation (Sanz et al. 1999; Sanz et al. 2000). The functional importance of p62/SQSTM1 in NFκB activation has been highlighted by the observation that its depletion severely abrogates NFκB activation by both TNFα and IL-1 (Sanz et al. 2000).

The sequence of p62/SQSTM1 was deposited in GenBank on Nov. 1, 2000 under accession number GI 4505570. This sequence was replaced on Apr. 4, 2002 with accession number GI 19923742. The differences in the two sequences were in the 5' and 3' untranslated regions and the sequence of the p62/SQSTM1 protein is the same. In the current application the sequence of wild type p62/SQSTM1 is from accession number GI 19923742 while in the priority application (U.S. provisional application Ser. No. 60/308,135, filed Jul. 30, 2001), the wild type 62 sequence was from accession number GI 4505570. As a result of the corrected sequence in the present application, the nucleotide position of the mutation associated with Paget disease was changed from nt 1227 to nt 1215. The position of the amino acid change (position 392) was unchanged. The sequence of the mutation in both the nucleotide (C→T) and amino acid sequence (Pro→Leu) sequence remains the same.

I. Nucleic Acid Molecules of the Invention

The present invention provides an isolated nucleic acid molecule comprising a sequence encoding an atypical protein kinase C-interacting protein having a molecular weight of approximately 62 kD. This protein is generally referred to as "p62/SQSTM1" herein. The terms "p62/SQSTM1", "p62" and "sequestosome 1" (or SQSTM1) are synonymous and may be used interchangeably in the present application (GenBank accession number GI 19923742; MIM number: 601530; and PubMed ID: 8650207).

The invention includes mutated forms of p62/SQSTM1 associated with Paget disease or any bone disease. In one embodiment, the mutated form has a nucleic acid sequence shown in SEQ.ID.NO.:3. The sequence shown in SEQ.ID.NO.:3 differs from SEQ.ID.NO.:1 (the wild type p62/SQSTM1 sequence) in that there is a T instead of a C at position 1215.

The term "isolated" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

In an embodiment of the invention, an isolated nucleic acid molecule is provided having a sequence which encodes p62/SQSTM1 having the amino acid sequence as shown in SEQ.ID.NO.:4.

In a preferred embodiment, the invention provides an isolated nucleic acid sequence comprising:

(a) a nucleic acid sequence as shown in SEQ.ID.NO.:3 wherein T can also be U;

(b) a nucleic acid sequence that is complimentary to a nucleic acid sequence of (a);

(c) a nucleic acid sequence that has substantial sequence homology to a nucleic acid sequence of (a) or (b);

(d) a nucleic acid sequence that is an analog of a nucleic acid sequence of (a), (b) or (c); or (e) a nucleic acid sequence that hybridizes to a nucleic acid sequence of (a), (b), (c) or (d) under stringent hybridization conditions.

The term "sequence that has substantial sequence homology" means those nucleic acid sequences which have slight or inconsequential sequence variations from the sequences in (a) or (b), i.e., the sequences function in substantially the same manner and can be used to detect, study or treat Paget disease of bone. The variations may be attributable to local mutations or structural modifications. Nucleic acid sequences having substantial homology include nucleic acid sequences having at least 65%, more preferably at least 85%, and most preferably 90-95% identity with the nucleic acid sequences as shown in SEQ.ID.NO.:1 or SEQ.ID.NO.:3.

The term "sequence that hybridizes" means a nucleic acid sequence that can hybridize to a sequence of (a), (b), (c) or (d) under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. For example, the following may be employed: 6.0× sodium chloride/sodium citrate (SSC) at about 45° C., followed by a wash of 2.0×SSC at 50° C.; 0.2×SSC at 50° C. to 65° C.; or 2.0×SSC at 44° C. to 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

The term "a nucleic acid sequence which is an analog" means a nucleic acid sequence which has been modified as compared to the sequence of (a), (b) or (c) wherein the modification does not alter the utility of the sequence as described herein. The modified sequence or analog may have improved properties over the sequence shown in (a), (b) or (c). One example of a modification to prepare an analog is to replace one of the naturally occurring bases (i.e. adenine, guanine, cytosine or thymidine) of the sequence shown in SEQ.ID.NO.:1 or 3, with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in SEQ.ID.NO.:1 or SEQ.ID.NO.:3. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

It will be appreciated that the invention includes nucleic acid molecules encoding truncations of proteins of the invention, and analogs and homologs of proteins of the invention and truncations thereof, as described below. It will further be appreciated that variant forms of nucleic acid molecules of the invention which arise by alternative splicing of an mRNA corresponding to a cDNA of the invention are encompassed by the invention.

Isolated and purified nucleic acid molecules having sequences which differ from the nucleic acid sequence of the invention due to degeneracy in the genetic code are also within the scope of the invention. Such nucleic acids encode functionally equivalent proteins but differ in sequence from the above mentioned sequences due to degeneracy in the genetic code.

An isolated nucleic acid molecule of the invention which comprises DNA can be isolated by preparing a labelled nucleic acid probe based on all or part of the nucleic acid sequences of the invention and using this labelled nucleic acid probe to screen an appropriate DNA library (e.g. a cDNA or genomic DNA library). For example, a genomic library isolated can be used to isolate a DNA encoding a novel protein of the invention by screening the library with the labelled probe using standard techniques. Nucleic acids isolated by screening of a cDNA or genomic DNA library can be sequenced by standard techniques.

An isolated nucleic acid molecule of the invention which is DNA can also be isolated by selectively amplifying a nucleic acid encoding a novel protein of the invention using the polymerase chain reaction (PCR) methods and cDNA or genomic DNA. It is possible to design synthetic oligonucleotide primers from the nucleic acid sequence of the invention for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Invitrogen, Carlsbad, Calif., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes a protein of the invention. For example, a cDNA can be cloned downstream of a bacteriophage promoter, (e.g., a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a novel protein of the invention may be accomplished by expressing the cDNA in an appropriate host cell by standard techniques, and testing the activity of the protein using the methods as described herein. A cDNA having the activity of a novel protein of the invention so isolated can be sequenced by standard techniques, such as dideoxynucleotide chain termination or Maxam-Gilbert chemical sequencing, to determine the nucleic acid sequence and the predicted amino acid sequence of the encoded protein.

The initiation codon and untranslated sequences of nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule which are more fully described herein. Preferably, an antisense sequence is constructed by inverting a region preceding the initiation codon or an unconserved region. In particular, the nucleic acid sequences contained in the nucleic acid molecules of the invention or a fragment thereof, may be inverted relative to its normal presentation for transcription to produce antisense nucleic acid molecules.

The invention also provides nucleic acids encoding fusion proteins comprising a novel protein of the invention and a selected protein, or a selectable marker protein (see below).

Also provided are portions of the nucleic acid sequence encoding fragments, functional domains or antigenic determinants of the p62/SQSTM1 or mutated p62/SQSTM1 protein. The present invention also provides for the use of portions of the sequence as probes and PCR primers for p62/SQSTM1 and related proteins and well as for determining functional aspects of the sequence.

One of ordinary skill in the art is now enabled to identify and isolate p62/SQSTM1 genes or cDNAs which are allelic variants of the disclosed p62/SQSTM1 sequence, using standard hybridization screening or PCR techniques.

II. Novel Proteins of the Invention

The invention further broadly contemplates an isolated atypical protein kinase C interacting protein having a molecular weight of approximately 62 kD. The term "p62/SQSTM1 protein" as used herein includes all homologs, analogs, fragments or derivatives of the p62/SQSTM1 protein. In one embodiment, the isolated p62/SQSTM1 has an amino acid sequence as shown in FIG. 3 (SEQ.ID.NO.:2).

The invention also includes mutated forms of p62/SQSTM1 that are diagnostic of Paget disease of bone or other bone diseases. In one embodiment, the mutated p62/SQSTM1 has an amino acid sequence shown in FIG. 3 or SEQ.ID.NO.:4. The sequence shown in SEQ.ID.NO.:4 differs from the wild type sequence shown in SEQ.ID.NO.:2 at amino acid position 392 where the proline in the wild type is changed to leucine in the mutated form.

Within the context of the present invention, a protein of the invention may include various structural forms of the primary protein which retain biological activity. For example, a protein of the invention may be in the form of acidic or basic salts or in neutral form. In addition, individual amino acid residues may be modified by oxidation or reduction.

In addition to the full length amino acid sequence, the protein of the present invention may also include fragments or truncations of the protein, and analogs, and homologs of the protein and truncations thereof as described herein. Truncated proteins or fragments may comprise peptides of at least 5, preferably 10 and more preferably 15 amino acid residues of the sequence shown in SEQ.ID.NO.:2 or 4.

The invention further provides polypeptides comprising at least one functional domain or at least one antigenic determinant of a p62/SQSTM1 protein or a mutated p62/SQSTM1 protein. Fragments of the p62/SQSTM1 protein that are useful include fragments that contain the proline to leucine mutation at position 392. The fragment of the p62/SQSTM1 protein may also include the ubiquitin associated domain at amino acid position 394-440.

Analogs of the protein of the invention and/or truncations thereof as described herein, may include, but are not limited to an amino acid sequence containing one or more amino acid substitutions, insertions, deletions and/or mutations. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequences of the invention. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequence of the p62/SQSTM1 protein. The deleted amino acids may or may not be contiguous. The lower limit. length of the resulting analog with a deletion mutation is about 10 amino acids, preferably 100 amino acids.

Analogs of a protein of the invention may be prepared by introducing mutations in the nucleotide sequence encoding the protein.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence of the p62/SQSTM1 protein, mutated p62/SQSTM1 protein and/or truncations thereof as described herein. Such homologs are proteins whose amino acid sequences are comprised of amino acid sequences that hybridize under stringent hybridization conditions (see discussion of stringent hybridization conditions herein) with a probe used to obtain a protein of the invention. Homologs of a protein of the invention will have the same regions which are characteristic of the protein.

A homologous protein includes a protein with an amino acid sequence having at least 70%, preferably 80-95% identity with the amino acid sequence of the p62/SQSTM1 protein or mutated p62/SQSTM1 protein.

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein to produce fusion proteins. For example, the p62/SQSTM1 cDNA sequence is inserted into a vector that contains a nucleotide sequence encoding another peptide (e.g. GST-glutathione succinyl transferase). The fusion protein is expressed and recovered from prokaryotic (e.g. bacterial or baculovirus) or eukaryotic cells. The fusion protein can then be purified by affinity chromatography based upon the fusion vector sequence and the p62/SQSTM1 protein obtained by enzymatic cleavage of the fusion protein.

The proteins of the invention (including truncations, analogs, etc.) may be prepared using recombinant DNA methods. Accordingly, nucleic acid molecules of the present invention having a sequence which encodes a protein of the invention may be incorporated according to procedures known in the art into an appropriate expression vector which ensures good expression of the protein. Possible expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence of the invention. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. Accordingly, the invention includes a host cell comprising a recombinant expression vector of the invention. The term "transformed host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Suitable host cells include a wide variety of prokaryotic and eukaryotic host cells. For example, the proteins of the invention may be expressed in bacterial cells such as *E. coli, Pseudomonas, Bacillus subtillus*, insect cells (using baculovirus), yeast cells or mammalian cells. Other suitable host cells can be found in Goeddel, Gene Expression Technology: Methods in Enzymology 185, Academic Press, San Diego, Calif. (1991).

As an example, to produce p62/SQSTM1 proteins recombinantly, for example, *E. coli* can be used using the T7 RNA polymerase/promoter system using two plasmids or by labeling of plasmid-encoded proteins, or by expression by infection with M13 Phage mGPI-2. *E. coli* vectors can also be used with Phage lamba regulatory sequences, by fusion protein vectors (e.g. lacZ and trpE), by maltose-binding protein fusions, and by glutathione-S-transferase fusion proteins.

Alternatively, the p62/SQSTM1 protein can be expressed in insect cells using baculoviral vectors, or in mammalian cells using vaccinia virus. For expression in mammalian cells, the cDNA sequence may be ligated to heterologous promoters, such as the simian virus (SV40) promoter in the pSV2 vector and introduced into cells, such as COS cells to achieve transient or long-term expression. The stable integration of the chimeric gene construct may be maintained in mammalian cells by biochemical selection, such as neomycin and mycophoenolic acid.

The p62/SQSTM1 DNA sequence can be altered using procedures such as restriction enzyme digestion, fill-in with DNA polymerase, deletion by exonuclease, extension by terminal deoxynucleotide transferase, ligation of synthetic or cloned DNA sequences, site-directed sequence alteration with the use of specific oligonucleotides together with PCR.

The cDNA sequence or portions thereof, or a mini gene consisting of a cDNA with an intron and its own promoter, is introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation. The endogenous p62/SQSTM1 gene promoter can also be used. Different promoters within vectors have different activities which alters the level of expression of the cDNA. In addition, certain promoters can also modulate function such as the glucocorticoid-responsive promoter from the mouse mammary tumor virus.

Some of the vectors listed contain selectable markers or neo bacterial genes that permit isolation of cells by chemical selection. Stable long-term vectors can be maintained in cells as episomal, freely replicating entities by using regulatory elements of viruses. Cell lines can also be produced which have integrated the vector into the genomic DNA. In this manner, the gene product is produced on a continuous basis.

Vectors are introduced into recipient cells by various methods including calcium phosphate, strontium phosphate, electroporation, lipofection, DEAE dextran, microinjection, or by protoplast fusion. Alternatively, the cDNA can be introduced by infection using viral vectors. p62/SQSTM1 proteins may also be isolated from cells or tissues, including mammalian cells or tissues, in which the protein is normally, expressed.

The protein may be purified by conventional purification methods known to those in the art, such as chromatography methods, high performance liquid chromatography methods or precipitation.

For example, anti-p62/SQSTM1 antibodies (as described below) may be used to isolate a p62/SQSTM1 protein, which is then purified by standard methods.

The proteins of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

III. Uses

The present invention includes all uses of the nucleic acid molecule and p62/SQSTM1 proteins of the invention including, but not limited to, the preparation of antibodies and antisense oligonucleotides, the preparation of experimental systems to study p62/SQSTM1 and mutated forms thereof, the isolation of substances that modulate p62/SQSTM1 expression and/or activity as well as the use of the p62/SQSTM1 nucleic acid sequences and proteins and modulators thereof in diagnostic and therapeutic applications. Some of the uses are further described below.

(a) Antibodies

The isolation of the p62/SQSTM1 protein and mutated p62/SQSTM1 protein enables the preparation of antibodies specific for p62/SQSTM1 and/or mutated p62/SQSTM1. Accordingly, the present invention provides an antibody that binds to a p62/SQSTM1 and/or mutated p62/SQSTM1 protein. Antibodies that only react with mutated p62/SQSTM1 may be used advantageously to diagnose Paget disease of bone or other bone diseases. Antibodies can be prepared which bind a distinct epitope in the mutated region of the protein.

Conventional methods can be used to prepare the antibodies. For example, by using a peptide of p62/SQSTM1, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the protein or peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for p62/SQSTM1 and/or mutated p62/SQSTM1 as described herein.

The term "antibody" as used herein is intended to include fragments thereof which also specifically react with p62/SQSTM1, or mutated p62/SQSTM1. Antibodies can be fragmented using conventional techniques and the fragments screened for utility in the same manner as described above. For example, F(ab')2 fragments can be generated by treating antibody with pepsin. The resulting F(ab')2 fragment can be further treated to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of p62/SQSTM1 antigens of the invention (See, for example, Morrison et al., Proc. Natl Acad. Sci. U.S.A. 81,6851 (1985); Takeda et al., Nature 314, 452 (1985), Cabilly et al., U.S. Pat. No. 4,816, 567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against p62/SQSTM1 proteins may also be generated by screening expression libraries encoding immunoglobulin genes, or portions thereof, expressed in bacteria with peptides produced from the nucleic acid molecules of p62/SQSTM1. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a SCID-hu mouse, for example the model developed by Genpharm, can be used to produce antibodies or fragments thereof.

(b) Antisense Oligonucleotides

Isolation of a nucleic acid molecule encoding p62/SQSTM1 and mutated p62/SQSTM1 enables the production of antisense oligonucleotides that can modulate the expression and/or activity of p62/SQSTM1 and/or mutated p62/SQSTM1.

Accordingly, the present invention provides an antisense oligonucleotide that is complimentary to a nucleic acid sequence encoding p62/SQSTM1 or mutated p62/SQSTM1. In one embodiment, the nucleic acid sequence encodes normal p62/SQSTM1 and is for example, as shown in SEQ.ID.NO.:1 or is as shown in GenBank under accession no. NM003900, XM035281 or GI 19923742.

In another embodiment, the nucleic acid sequence encodes a mutated p62/SQSTM1 that is associated with Paget disease or another bone disease. Preferably the nucleic acid sequence is as shown in SEQ.ID.NO.:3.

The term "antisense oligonucleotide" as used herein means a nucleotide sequence that is complimentary to its target.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The antisense oligonucleotides may be introduced into tissues or cells using techniques in the art including vectors (retroviral vectors, adenoviral vectors and DNA virus vectors) or physical techniques such as microinjection. The antisense oligonucleotides may be directly administered in vivo or may be used to transfect cells in vitro which are then administered in vivo. In one embodiment, the antisense oligonucleotide may be delivered to macrophages and/or endothelial cells in a liposome formulation.

(c) Diagnostic Assays

The finding by the present inventors that mutated p62/SQSTM1 is involved in Paget disease of bone allows development of diagnostic assays for detecting Paget disease of bone or other bone diseases.

Accordingly, the present invention provides a method of detecting a condition associated with a mutated p62/SQSTM1 protein comprising assaying a sample for (a) a nucleic acid molecule encoding a mutated p62/SQSTM1 protein or a fragment thereof or (b) a mutated p62/SQSTM1 protein or a fragment thereof. The mutated p62/SQSTM1 protein preferably has the sequence shown in SEQ.ID.NO.:4. In one embodiment, the condition associated with the mutated p62/SQSTM1 protein is Paget disease of bone.

(i) Nucleic Acid Molecules

The nucleic acid molecules encoding mutated p62/SQSTM1 as described herein or fragments thereof, allow those skilled in the art to construct nucleotide probes for use in the detection of nucleotide sequences encoding mutated p62/SQSTM1 or fragments thereof in samples, preferably biological samples such as cells, tissues and bodily fluids. The probes can be useful in detecting the presence of a condition associated with mutated p62/SQSTM1 or monitoring the progress of such a condition. Such conditions include Paget disease of bone.

Accordingly, the present invention provides a method for detecting a nucleic acid molecule encoding a mutated p62/SQSTM1 in a sample comprising contacting the sample with a nucleotide probe capable of hybridizing with the nucleic acid molecule to form a hybridization product, under conditions which permit the formation of the hybridization product, and assaying for the hybridization product.

The nucleotide probe used in the diagnostic assay will hybridize with mutated p62/SQSTM1 (containing the proline to leucine mutation at position 392) but not with wild type p62/SQSTM1. Example of probes that may be used in the above method include fragments of the nucleic acid sequences shown in FIG. 3 or SEQ.ID.NO.:3. A nucleotide probe may be labelled with a detectable substance such as a radioactive label which provides for an adequate signal and has sufficient half-life such as 32P, 3H, 14C or the like. Other detectable substances which may be used include antigens that are recognized by a specific labelled antibody, fluorescent compounds, enzymes, antibodies specific for a labelled antigen, and chemiluminescence. An appropriate label may be selected having regard to the rate of hybridization and binding of the probe to the nucleic acid to be detected and the amount of nucleic acid available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleotide probes may be used to detect genes, preferably in human cells, that hybridize to the nucleic acid molecule of the present invention preferably, nucleic acid molecules which hybridize to the nucleic acid molecule of the invention under stringent hybridization conditions as described herein.

In one embodiment, the hybridization assay can be a Southern analysis where the patient sample is tested for a DNA sequence that hybridizes with a mutated p62/SQSTM1 specific probe. In another embodiment, the hybridization assay can be a Northern analysis where the patient sample is tested for an RNA sequence that hybridizes with a mutated p62/SQSTM1 specific probe. Southern and Northern analyses may be performed using techniques known in the art (see for example, Current Protocols in Molecular Biology, Ausubel, F. et al., eds., John Wiley & Sons).

Nucleic acid molecules encoding a mutated p62/SQSTM1 protein can be selectively amplified in a sample using the polymerase chain reaction (PCR) methods and cDNA or genomic DNA. It is possible to design synthetic oligonucleotide primers from the nucleotide sequence shown in SEQ.ID.NO.:3 for use in PCR. A nucleic acid can be amplified from cDNA or genomic DNA using oligonucleotide primers and standard PCR amplification techniques. The amplified nucleic acid can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

Patients may be screened routinely using probes to detect the presence of a mutant p62/SQSTM1 gene by a variety of techniques. Genomic DNA used for the diagnosis may be obtained from body cells, such as those present in the blood, tissue biopsy, surgical specimen, or autopsy material. The DNA may be isolated and used directly for detection of a specific sequence or may be PCR amplified prior to analysis. RNA or cDNA may also be used. To detect a specific DNA sequence hybridization using specific oligonucleotides, direct DNA sequencing, restriction enzyme digest, RNase protection, chemical cleavage, and ligase-mediated detection are all methods which can be utilized. Oligonucleotides specific to mutant sequences can be chemically synthesized and labelled radioactively with isotopes, or non-radioactively using biotin tags, and hybridized to individual DNA samples immobilized on membranes or other solid-supports by dot-blot or transfer from gels after electrophoresis. The presence or absence of these mutant sequences is then visualized using methods such as autoradiography, fluorometry, or colorimetric reaction. Suitable PCR primers can be generated which are useful for example in amplifying portions of the subject sequence containing identified mutations.

Direct DNA sequencing reveals sequence differences between normal and mutant p62/SQSTM1 DNA. Cloned DNA segments may be used as probes to detect specific DNA segments. PCR can be used to enhance the sensitivity of this method. PCR is an enzymatic amplification directed by sequence-specific primers, and involves repeated cycles of heat denaturation of the DNA, annealing of the complementary primers and extension of the annealed primer with a DNA polymerase. This results in an exponential increase of the target DNA.

Other nucleotide sequence amplification techniques may be used, such as ligation-mediated PCR, anchored PCR and enzymatic amplification as would be understood by those skilled in the art.

Sequence alterations may also generate fortuitous restriction enzyme recognition sites that are revealed by the use of appropriate enzyme digestion followed by gel-blot hybridization. DNA fragments carrying the site (normal or mutant) are detected by their increase or reduction in size, or by the increase or decrease of corresponding restriction fragment numbers. Genomic DNA samples may also be amplified by PCR prior to treatment with the appropriate restriction enzyme and the fragments of different sizes are visualized under UV light in the presence of ethidium bromide after gel electrophoresis.

Genetic testing based on DNA sequence differences may be achieved by detection of alteration in electrophoretic mobility of DNA fragments in gels. Small sequence deletions and insertions can be visualized by high-resolution gel electrophoresis. Small deletions may also be detected as changes in the migration pattern of DNA heteroduplexes in non-denaturing gel electrophoresis. Alternatively, a single base substitution mutation may be detected based on differential primer length in PCR. The PCR products of the normal and mutant gene could be differentially detected in acrylamide gels.

Nuclease protection assays (S1 or ligase-mediated) also reveal sequence changes at specific locations. Alternatively, to confirm or detect a polymorphism restriction mapping changes ligated PCR, ASO, REF-SSCP and SSCP may be used. Both REF-SSCP and SSCP are mobility shift assays that are based upon the change in conformation due to mutations.

DNA fragments may also be visualized by methods in which the individual DNA samples are not immobilized on membranes. The probe and target sequences may be in solution or the probe sequence may be immobilized. Autoradiography, radioactive decay, spectrophotometry, and fluorometry may also be used to identify specific individual genotypes.

According to an embodiment of the invention, the portion of the DNA segment that is informative for a mutation can be amplified using PCR. For example, to detect for the proline to leucine mutation at amino acid position 392, the DNA around nucleotide position 1215 can be amplified. The DNA segment immediately surrounding a specific mutation acquired from peripheral blood or other tissue samples from an individual can be screened using constructed oligonucleotide primers. This region would then be amplified by PCR, the products separated by electrophoresis, and transferred to membrane. Labeled probes are then hybridized to the DNA fragments and autoradiography performed.

(ii) Proteins

The mutated p62/SQSTM1 protein may be detected in a sample using antibodies that bind to the protein as described in detail above. Accordingly, the present invention provides a method for detecting a mutated p62/SQSTM1 protein comprising contacting the sample with an antibody that binds to mutated p62/SQSTM1 which is capable of being detected after it becomes bound to the mutated p62/SQSTM1 in the sample.

Antibodies specifically reactive with mutated p62/SQSTM1, or derivatives thereof, such as enzyme conjugates or labeled derivatives, may be used to detect mutated p62/SQSTM1 in various biological materials, for example they may be used in any known immunoassays which rely on the binding interaction between an antigenic determinant of mutated p62/SQSTM1, and the antibodies. Examples of such assays are radioimmunoassays, enzyme immunoassays (e.g. ELISA), immunofluorescence, immunoprecipitation, latex agglutination, hemagglutination and histochemical tests. Thus, the antibodies may be used to detect and quantify mutated p62/SQSTM1 in a sample in order to determine its role in particular cellular events or pathological states, and to diagnose and treat such pathological states, preferably Paget disease of bone.

In particular, the antibodies of the invention may be used in immuno-histochemical analyses, for example, at the cellular and sub-subcellular level, to detect mutated p62/SQSTM1, to localise it to particular cells and tissues and to specific subcellular locations, and to quantitate the level of expression.

Cytochemical techniques known in the art for localizing antigens using light and electron microscopy may be used to detect mutated p62/SQSTM1. Generally, an antibody of the invention may be labelled with a detectable substance and mutated p62/SQSTM1 may be localised in tissue based upon the presence of the detectable substance. Examples of detectable substances include various enzymes, fluorescent materials, luminescent materials and radioactive materials. Examples of suitable enzymes include horseradish peroxidase, biotin, alkaline phosphatase, $\beta$-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine I-125, I-131 or 3-H. Antibodies may also be coupled to electron dense substances, such as ferritin or colloidal gold, which are readily visualised by electron microscopy.

Indirect methods may also be employed in which the primary antigen-antibody reaction is amplified by the introduction of a second antibody, having specificity for the antibody reactive against mutated p62/SQSTM1. By way of example, if the antibody having specificity against mutated p62/SQSTM1 is a rabbit IgG antibody, the second antibody may be goat anti-rabbit gamma-globulin labelled with a detectable substance as described herein.

Where a radioactive label is used as a detectable substance, mutated p62/SQSTM1 may be localized by autoradiography. The results of autoradiography may be quantitated by determining the density of particles in the autoradiographs by various optical methods, or by counting the grains.

(d) Experimental Systems

Eukaryotic expression systems can be used for many studies of the p62/SQSTM1 gene and gene product(s) including the production of large amounts of the normal and mutant protein for isolation and purification, to use cells expressing the p62/SQSTM1 or mutated p62/SQSTM1 protein as a functional assay system for antibodies generated against the protein or to test effectiveness of pharmacological agents, to study the function of the normal complete protein, specific portions of the protein, or of naturally occurring and artificially produced mutant proteins.

Using the techniques mentioned, the expression vectors containing the p62/SQSTM1 or mutated p62/SQSTM1 cDNA sequence or portions thereof can be introduced into a variety of mammalian cells from other species or into non-mammalian cells.

The recombinant cloning vector, according to this invention, comprises the selected DNA of the DNA sequences of this invention for expression in a suitable host. The DNA is operatively linked in the vector to an expression control sequence in the recombinant DNA molecule so that p62/SQSTM1 protein can be expressed. The expression control sequence may be selected from the group consisting of sequences that control the expression of genes of prokaryotic or eukaryotic cells and their viruses and combinations thereof. The expression control sequence may be selected from the group consisting of the lac system, the trp system, the tac system, the trc system, major operator and promoter regions of phage lambda, the control region of the fd coat protein, early and late promoters of SV40, promoters derived from polyoma, adenovirus, retrovirus, baculovirus, simian virus, 3-phosphoglycerate kinase promoter, yeast acid phosphatase promoters, yeast alpha-mating factors and combinations thereof.

Expression of the p62/SQSTM1 gene in heterologous cell systems may also be used to demonstrate structure-function relationships as well as to provide cell lines for the purposes of drug screening. p62/SQSTM1 DNA sequence into a plasmid expression vector to transfect cells is a useful method to test the proteins influence on various cellular biochemical parameters including the identification of substrates as well as activators and inhibitors of the gene. Plasmid expression vectors containing either the entire coding sequence for p62/SQSTM1, or for portions thereof, can be used in in vitro mutagenesis experiments that will identify portions of the protein crucial for function.

The DNA sequence can be manipulated in studies to understand the expression of the gene and its product. The changes in the sequence may or may not alter the expression pattern in terms of relative quantities, tissue-specificity and functional properties.

The invention also provides methods for examining the function of the p62/SQSTM1 and mutated p62/SQSTM1 protein encoded by the nucleic acid molecules of the invention. Cells, tissues, and non-human animals lacking in expression or partially lacking in expression of the protein may be developed using recombinant molecules of the invention having specific deletion or insertion mutations in the nucleic acid molecule of the invention. A recombinant molecule may be used to inactivate or alter the endogenous gene by homologous recombination, and thereby create a deficient cell, tissue or animal. Such a mutant cell, tissue or animal may be used to define specific cell populations, developmental patterns and in vivo processes, normally dependent on the protein encoded by the nucleic acid molecule of the invention.

To confirm the importance of the p62/SQSTM1 protein in Paget disease of bone, a p62/SQSTM1 knockout mouse can be prepared. By way of example, a targeted recombination strategy may be used to inactivate the endogenous p62/SQSTM1 gene. A gene which introduces stop codons in all reading frames and abolishes the biological activity of the protein may be inserted into a genomic copy of the protein. The mutated fragment may be introduced into embryonic stem cells and colonies may be selected for homologous recombination with positive (neomycin)/negative (gancyclovir, thymidine kinase) resistance genes. To establish germ line transmission, two clones carrying the disrupted gene on one allele may be injected into blastocyts of C57Bl/6 mice and transferred into B6/SJL foster mothers. Chimeras may be mated to C57Bl/6 mice and progeny analysed to detect animals homozygous for the mutation (p62/SQSTM1 −/−). The effects of the mutation on Paget disease of bone or other conditions of the bone in comparison to non-mutated controls may be determined, and the survival and histologic pattern of disease may be analyzed.

The UBA domain is conserved among other species (mouse and rat), including the P392 residue. Accordingly, the invention also provides for the construction of a non-human animal carrying the point mutation encoding for the P392L mutated p62/SQSTM1 protein. Such a mutant cell, tissue or animal may be used as a model for bone disease, preferably Paget disease of bone.

(e) p62/SQSTM1 Modulators

In addition to antibodies and antisense oligonucleotides described above, other substances that modulate p62/SQSTM1 expression or activity may also be identified, as well as substances that modulate mutated forms of p62/SQSTM1.

(i) Substances that Bind p62/SQSTM1

Substances that affect p62/SQSTM1 activity can be identified based on their ability to bind to p62/SQSTM1 and/or mutated p62/SQSTM1.

Substances which can bind with the p62/SQSTM1 of the invention may be identified by reacting the p62/SQSTM1 with a substance which potentially binds to p62/SQSTM1, and assaying for complexes, for free substance, or for non-complexed p62/SQSTM1, or for activation of p62/SQSTM1. In particular, a yeast two hybrid assay system may be used to identify proteins which interact with p62/SQSTM1 (Fields, S. and Song, O., 1989, Nature, 340:245-247). Systems of analysis which also may be used include ELISA.

Accordingly, the invention provides a method of identifying substances which can bind with p62/SQSTM1, comprising the steps of:

(a) reacting p62/SQSTM1 and a test substance, under conditions which allow for formation of a complex between the p62/SQSTM1 and the test substance, and (b) assaying for complexes of p62/SQSTM1 and the test substance, for free substance or for non complexed p62/SQSTM1, wherein the presence of complexes indicates that the test substance is capable of binding p62/SQSTM1.

The p62/SQSTM1 protein used in the assay may have the amino acid sequence shown in SEQ.ID.NO.:2 or SEQ.ID.NO.:4 or may be a fragment, analog, derivative, homolog or mimetic thereof as described herein.

Conditions which permit the formation of substance and p62/SQSTM1 complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against p62/SQSTM1 or the substance, or labelled p62/SQSTM1, or a labelled substance may be utilized. The antibodies, proteins, or substances may be labelled with a detectable substance as described above.

p62/SQSTM1, or the substance used in the method of the invention may be insolubilized. For example, p62/SQSTM1 or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized protein or substance may be prepared by reacting the material with a suitable insoluble carrier using known chemical or physical methods, for example, cyanogen bromide coupling.

The proteins or substance may also be expressed on the surface of a cell using the methods described herein.

The invention also contemplates assaying for an antagonist or agonist of the action of p62/SQSTM1.

It will be understood that the agonists and antagonists that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of p62/SQSTM1. Thus, the invention may be used to assay for a substance that competes for the same binding site of p62/SQSTM1.

(ii) Peptide Mimetics

The present invention also includes peptide mimetics of the p62/SQSTM1 and mutated p62/SQSTM1 proteins of the invention. For example, a peptide derived from a the mutated domain of p62/SQSTM1 will interact directly or indirectly with an associated molecule in such a way as to mimic the native binding of the mutated protein. The peptide mimetic may be derived from the UBA domain of p62/SQSTM1. Such peptides may include competitive inhibitors, enhancers, peptide mimetics, and the like. All of these peptides as well as molecules substantially homologous, complementary or otherwise functionally or structurally equivalent to these peptides may be used for purposes of the present invention.

"Peptide mimetics" are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a peptide of the invention.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Peptides of the invention may also be used to identify lead compounds for drug development. The structure of the peptides described herein can be readily determined by a number of methods such as NMR and X-ray crystallography. A comparison of the structures of peptides similar in sequence, but differing in the biological activities they elicit in target molecules can provide information about the structure-activity relationship of the target. Information obtained from the examination of structure-activity relationships can be used to design either modified peptides, or other small molecules or lead compounds that can be tested for predicted properties as related to the target molecule. The activity of the lead compounds can be evaluated using assays similar to those described herein.

Information about structure-activity relationships may also be obtained from co-crystallization studies. In these studies, a peptide with a desired activity is crystallized in association with a target molecule, and the X-ray structure of the complex is determined. The structure can then be compared to the structure of the target molecule in its native state, and information from such a comparison may be used to design compounds expected to possess.

(iii) Drug Screening Methods

In accordance with one embodiment, the invention enables a method for screening candidate compounds for their ability to increase or decrease the activity of the mutated p62/SQSTM1 protein. The method comprises providing an assay system for assaying p62/SQSTM1 activity, assaying the activity in the presence or absence of the candidate or test compound and determining whether the compound has increased or decreased p62/SQSTM1 activity. Such compounds may be useful in treating Paget disease of bone.

Accordingly, the present invention provides a method for identifying a compound that affects mutated p62/SQSTM1 protein activity or expression comprising:
(a) incubating a test compound with a p62/SQSTM1 protein or a nucleic acid encoding a p62/SQSTM1 protein; and
(b) determining an amount of p62/SQSTM1 protein activity or expression and comparing with a control (i.e. in the absence of the test substance), wherein a change in the p62/SQSTM1 protein activity or expression as compared to the control indicates that the test compound has an effect on p62/SQSTM1 protein activity or expression.

In accordance with a further embodiment, the invention enables a method for screening candidate compounds for their ability to increase or decrease expression of a p62/SQSTM1 protein. The method comprises putting a cell with a candidate compound, wherein the cell includes a regulatory region of a p62/SQSTM1 gene operably joined to a reporter gene coding region, and detecting a change in expression of the reporter gene.

In one embodiment, the present invention enables culture systems in which cell lines which express the mutated p62/SQSTM1 gene are incubated with candidate compounds to test their effects on mutated p62/SQSTM1 expression. Such culture systems can be used to identify compounds which upregulate or downregulate p62/SQSTM1 expression or its function, through the interaction with other proteins.

Such compounds can be selected from protein compounds, chemicals and various drugs that are added to the culture medium. After a period of incubation in the presence of a selected test compound(s), the expression of mutated p62/SQSTM1 can be examined by quantifying the levels of p62/SQSTM1 mRNA using standard Northern blotting procedure, as described in the examples included herein, to determine any changes in expression as a result of the test compound. Cell lines transfected with constructs expressing p62/SQSTM1 can also be used to test the function of compounds developed to modify the protein expression.

(f) Therapeutic Uses

As previously discussed, the p62/SQSTM1 of the invention is likely involved in Paget disease of bone and other related diseases of the bone including osteoporosis. Accordingly, the present invention provides a method of treating a bone disease comprising of administering to a cell or animal in need thereof, an effective amount of agent that modulates p62/SQSTM1 expression and/or activity. The present invention also provides a use of an agent that modulates p62/SQSTM1 expression and/or activity to treat a bone disease or to prepare a medicament to treat a bone disease.

The term "agent that modulates p62/SQSTM1 expression and/or activity" means any substance that can alter the expression and/or activity of the mutated p62/SQSTM1 found in the patient to be consistent with the wild type p62/SQSTM1. Examples of agents which may be used to include administering: a nucleic acid molecule encoding wild type p62/SQSTM1; the wild type p62/SQSTM1 protein as well as fragments, analogs, derivatives or homologs thereof; antibodies; antisense nucleic acids; peptide mimetics; and substances isolated using the screening methods described herein that can correct the mutation to result in p62/SQSTM1 levels and/or function consistent with a person without the disease.

The term "effective amount" as used herein means an amount effective, at dosages and for periods of time necessary to achieve the desired results.

The term "animal" as used herein includes all members of the animal kingdom, including humans.

In one embodiment, the invention provides a method of treating Paget disease of bone by administering to a cell or animal an effective amount of an agent that modulates the expression or the biological activity of the mutated p62/SQSTM1 protein. The present invention also provides a use of an effective amount of an agent that modulates the expression or the biological activity of the mutated p62/SQSTM1 protein to treat Paget disease of bone or to prepare a medicament to treat Paget disease of bone. Substances that inhibit the activity of mutated p62/SQSTM1 include peptide mimetics, p62/SQSTM1 antagonists and certain antibodies to p62/SQSTM1. Substances that inhibit the expression of the mutated p62/SQSTM1 gene include antisense oligonucleotides to a mutated p62/SQSTM1 nucleic acid sequence.

All of the diseases of bone occur as a consequence of the effects of the disease process on the cellular events in the normal bone remodelling cycle. The adult skeleton is in a dynamic state, being continually broken down and reformed by the coordinated actions of osteoclasts and osteoblasts on trabecular surfaces and in haversian systems (cortical bone). Current concepts of the bone remodelling or turnover are based on the morphologic observations of Frost and colleagues (Hattner R, Etker B N, Frost H M. Suggested sequential mode of control of changes in cell behaviour in adult bone remodeling. Nature 1965; 206 (983): 489-490.), who observed that bone formation in human adults occurred almost exclusively at sites that had recently undergone osteoclastic resorption. This turnover or remodelling of bone occurs in focal and discrete packets throughout the skeleton. It is now recognized that the remodelling of each packet takes a finite period of time (estimated to be about 3-4 months). The remodelling which occurs in each packet (called a bone remodelling unit by Frost) is geographically and chronologically separated from other packets of remodelling. This suggests that activation of the frequence (also called activation frequency) of cellular events responsible for remodelling is locally controlled, possibly by an autoregulatory mechanism, perhaps by autocrine or paracrine factors generated in the bone microenvironment. The sequence is always the same—osteoclastic bone resorption (10 days) followed by osteoblastic bone formation (3 months) to repair the defect. The new bone that is formed is called a bone structural unit (BSU) (Frost H M. Dynamics of the bone remodelling. In: Bone Biodynamics. Boston: Little & Brown, 1964: 315.).

Osteoclast activation is the initial step in the remodelling sequence. Osteoclasts are activated in specific focal sites by mechanisms that are still not understood. This period is followed by repair of the resorption defect by a team of osteoblasts, which are attracted to the site of the resorption defect and then proceed to make new bone. The complete sequence of the cellular events that occur at the bone surface during the remodeling process has been described in detail by Baron et al (Baron R, Vignery A, Horowitz M. Lymphocytes, macrophages and the regulation of bone remodeling. In: Bone and Mineral Research, Peck W A ed. Amsterdam, Elsevier, 1984: 175-243.) from studies on the alveolar bone of the rat, and by Boyce et al (Boyce B F, Yates A J P, Mundy G R. Bolus injections of recombinant human interleukin-1 cause transient hypocalcemia in normal mice. Endocrinology 1989; 125:2780-3.) from studies of the calvarial bone of the mouse. The cellular events that occur in these models are similar to those in adult human bone. In normal conditions bone resorption and bone formation are coupled and in balance. It is useful to draw a distinction between skeletal balance and the coupling of bone formation to bone resorption. Uncoupling implies the dissociation of these two processes; either the creation of resorption cavities without subsequent attraction of osteoblasts, as is sometimes seen in neoplasia such as multiple myeloma, or conversely, the deposition of new bone at sites other than sites of previous resorption. The latter occurs conspicuously in various tumors such as metastatic bone disease due to breast or prostatic carcinoma. The extent to which uncoupled resorption or formation occurs in the healthy adult is not known, but it is likely to be a very small component of turnover (Jaworski Z F G, Meunier P J and Frost H M. Observations on two types of resorption cavities in human lamellar cortical bone. Clin Orthop 1972; 83: 279-285.), perhaps principally in the repair of microfractures.

In the case of Paget disease of bone, there is little evidence for uncoupled bone formation even in the presence of dense osteosclerosis. When new bone formed is woven, like in Paget disease of bone, trabecular osteosclerosis may arise without necessarily an increase in the amount of collagen (or calcium) due to the loosely packed collagen (woven bone rather than the well organized normal lamellar bone). When the balance between bone formation and resorption is disturbed, each remodelling sequence results in a finite gain (or positive balance, like in Paget disease of bone, and, primary and secondary hyperparathyroidism) or loss of bone (negative balance, like in postmenopausal osteoporosis, male osteoporosis, glucocorticoid-induced osteoporosis, and algodystrophy). The rate of gain or loss will be amplified in proportion to the frequency of activation of new remodelling units. The activation frequency is dramatically increased but only in bone affected with the Paget disease of bone whereas it appears normal in unaffected bone sites. In other bone diseases the activation frequency is increased over the entire skeleton. A better understanding of the mechanisms involved in the focal increase in activation frequency and the positive balance observed in Paget disease of bone therefore will lead to the finding of innovative therapies targeted to modulations of the bone remodelling processes in other metabolic bone diseases associated with a universal increase of the activation frequency over the entire skeleton: primary and secondary hyperparathyroidism, postmenopausal osteoporosis, glucocorticoid-induced osteoporosis, and algodystrophy. Since p62/SQSTM1 is linked to Paget disease of bone, it will be a potential target for therapeutic interventions in other metabolic bone diseases.

Therefore, the inventors claim that mutations in the p62/SQSTM1 gene may also be associated with other bone disorders, including osteoporosis. Accordingly, the therapeutic methods of the invention may be used to treat any bone disease (including Paget disease of bone and osteoporosis).

In accordance with another embodiment, the present invention enables gene therapy as a potential therapeutic approach to a bone disease, in which normal copies of the p62/SQSTM1 gene are introduced into patients to successfully code for normal p621SQSTM1 protein in several different affected cell types.

Retroviral vectors can be used for somatic cell gene therapy especially because of their high efficiency of infection and stable integration and expression. The targeted cells however must be able to divide and the expression of the levels of normal protein should be high. The full length normal p62/SQSTM1 gene can be cloned into a retroviral vector and driven from its endogenous promoter or from the retroviral long terminal repeat or from a promoter specific for the target cell type of interest (such as lymphoid cells). Other viral vectors which can be used include adeno-associated virus, vaccinia virus, bovine papilloma virus, or a herpesvirus such as Epstein-Barr virus. Gene transfer could also be achieved using non-viral means requiring infection in vitro. This would include calcium phosphate, DEAE dextran, electroporation, cationic or anionic lipid formulations (liposomes) and protoplast fusion. Although these methods are available, many of these are lower efficiency.

Anti-sense based strategies can be employed to inhibit mutated p62/SQSTM1 gene function and as a basis for therapeutic drug design. The principle is based on the hypothesis that sequence specific suppression of gene expression can be achieved by intracellular hybridization between mRNA and a complementary anti-sense species. It is possible to synthesize anti-sense strand nucleotides that bind the sense strand of RNA or DNA with a high degree of specificity. The formation of a hybrid RNA duplex may interfere with the processing/transport/translation and/or stability of a target mRNA.

Hybridization is required for an antisense effect to occur. Antisense effects have been described using a variety of approaches including the use of antisense oligonucleotides, injection of antisense RNA, DNA and transfection of antisense RNA expression vectors.

Therapeutic antisense nucleotides can be made as oligonucleotides or expressed nucleotides. Oligonucleotides are short single strands of DNA which are usually 15 to 20 nucleic acid bases long. Expressed nucleotides are made by an expression vector such as an adenoviral, retroviral or plasmid vector. The vector is administered to the cells in culture, or to a patient, whose cells then make the antisense nucleotide. Expression vectors can be designed to produce antisense RNA, which can vary in length from a few dozen bases to several thousand.

Antisense effects can be induced by control (sense) sequences. The extent of phenotypic changes are highly variable. Phenotypic effects induced by antisense are based on changes in criteria such as biological endpoints, protein levels, protein activation measurement and target mRNA levels.

(g) Pharmaceutical Compositions

The above described substances including nucleic acids encoding p62/SQSTM1 and mutated p62/SQSTM1, p62/SQSTM1 and mutated p62/SQSTM1 proteins, antibodies, and antisense oligonucleotides as well as other agents that modulate p62/SQSTM1 and/or mutated p62/SQSTM1 may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals.

Administration of a therapeutically active amount of pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of the substance to elicit a desired response in the individual. Dosage regimes may be adjusted to provide the optimum therapeutic response. For example, several divided doses may be administered daily or the dose may be proportionally reduced as indicated by the exigencies of the therapeutic situation.

An active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound. If the active substance is a nucleic acid encoding, for example, a modified p62/SQSTM1 it may be delivered using techniques known in the art.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985) or Handbook of Pharmaceutical Additives (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456. As will also be appreciated by those skilled, administration of substances described herein may be by an inactive viral carrier.

(h) Kits

The reagents suitable for carrying out the methods of the invention may be packaged into convenient kits providing the necessary materials, packaged into suitable containers. Such kits may include all the reagents required to detect a nucleic acid molecule or protein of the invention in a sample by means of the methods described herein, and optionally suitable supports useful in performing the methods of the invention. The kits can be useful in detecting Paget disease of bone or other bone diseases.

In one embodiment of the invention, the kit includes primers which are capable of amplifying a nucleic-acid molecule of the invention or a predetermined oligonucleotide fragment thereof, all the reagents required to produce the amplified nucleic acid molecule or predetermined fragment thereof in the polymerase chain reaction, and means for assaying the amplified sequences.

In one embodiment, the primers can amplify a nucleic acid encoding a mutated p62/SQSTM1 protein, preferably the protein of SEQ.ID.NO.:4. In such a case the primer will amplify the region surrounding nucleotide 1215 in the sequence shown in SEQ.ID.NO.:3.

The kit may also include restriction enzymes to digest the PCR products. In another embodiment of the invention the kit contains a nucleotide probe which hybridizes with a nucleic acid molecule of the invention, reagents required for hybridization of the nucleotide probe with the nucleic acid molecule, and directions for its use. In a further embodiment of the invention, the kit includes antibodies of the invention and reagents required for binding of the antibody to a mutated p62/SQSTM1 protein of the invention in a sample.

The methods and kits of the present invention may be used to detect Paget disease of bone. Samples which may be tested include bodily materials such as blood, urine, serum, tears, saliva, feces, tissues, cells and the like. In addition to human samples, samples may be taken from mammals such as non-human primates, etc.

Before testing a sample in accordance with the methods described herein, the sample may be concentrated using techniques known in the art, such as centrifugation and filtration. For the hybridization and/or PCR-based methods described herein, nucleic acids may be extracted from cell extracts of the test sample using techniques known in the art.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present invention:

EXAMPLES

Example 1

The inventors have identified a mutated atypical protein kinase C-interacting protein p62/sequestosome 1 (p62/SQSTM1) as the gene causing Paget disease of bone.

General Strategy

A region on chromosome 5 band q35 to the telomere of the human genome which contains the genetic locus PDB3, which causes Paget disease of bone, has been confined within an interval of 6 cM. This PDB3 locus which contains the p62/SQSTM1 gene was identified using a variety of genetic techniques, including genetic mapping as defined above. Based upon studies of large extended families ("kindred or pedigrees") with multiple cases of Paget disease of bone as well as approximately 100 sporadic patients affected by the disorder, the chromosomal region containing the disease gene was refined to approximately 2 million nucleotides on chromosome 5q35. The region which contains the p62/SQSTM1 was physically bounded by CA5-5 and CA5-26. (The inventors have developed their own dinucleotide markers starting from sequences available publicly).

Population Resources

To identify the molecular basis of Paget disease of bone, the inventors conducted genetic linkage and haplotype studies in French-Canadian families. Kindreds originating from this population are particularly well suited for such studies (Morissette et al. 1995; Morissette et al. 1998). Indeed, for social and. linguistic reasons, this population has maintained for the last three centuries a demographic growth without immigration and until recently, a high birth rate with large sibships, containing 10 to 15 sibs per generation (Bouchard and Braekeleer 1991). Pedigree reconstruction was also facilitated by their conservation of genealogical records, including birth, marriage and death certificates that go back to the first immigrants. To counteract the genetic heterogeneity of Paget disease of bone, the inventors exploited these attributes and undertook the systematic screening of large French-Canadian families affected by the disorder.

The inventors recruited 24 French-Canadian families with at least two affected first-degree relatives, for a total of 554 individuals, including 56 spouses. These kindreds were of different sizes and complexities. Eight of them comprised between 30 and 71 individuals and 14 displayed Paget disease of bone over two generations. Twelve pedigrees came from the same geographic area.

Out of these 554 individuals, 105 were diagnosed with Paget disease of bone. Age at diagnosis ranged from 29 to 89 years old, with a mean age of 58 years old. The majority of these patients were diagnosed at 60 years of age or older (63/105; 60%) while only a small number were diagnosed before 40 years of age (3/105; 2.9%). Paget disease of bone was segregating as an autosomal dominant trait with an incomplete age-dependent penetrance within the pedigrees.

To identify p62/SQSTM1 as the mutated gene causing Paget disease of bone, the inventors also studied 112 patients affected by the disorder. These patients were recruited as sporadic cases.

Genetic Mapping and Confinement of Paget Disease of Bone at the PDB3 Locus on Chromosome 5q35-qter Genetic markers useful in searching for a genetic locus associated with a disease can be selected on an ad hoc basis by densely covering a specific chromosome, or a detailed analysis of a specific region of a chromosome. The inventors performed genetic linkage analysis in 24 French-Canadian kindreds in which the disorder was segregating as an autosomal dominant trait. Two novel loci for Paget disease of bone were mapped at chromosome 5q35-qter and at chromosome 5q31. These two loci have been named PDB3 and PDB4, respectively.

Once linkage has been established, markers that flank the disease locus, i.e. one or more markers proximal to the disease locus, and one or more markers distal to the disease locus, need to be identified. The PDB3 locus was defined by marker AFM 137×f6 at locus D5S469 and the telomere. To further refine the genetic interval, 11 dinucleotide polymorphic markers were designed within the genetic interval. These markers were designed by searching in silico the draft of the Human Genome Project available electronically at http://www.ncbi.nlm.nih.gov/ for dinucleotide repeats. Synthesis of appropriate primers around these repeats was performed to amplify the dinucleotides. The primers used to genotype the polymorphic dinucleotide markers designed to confine the PDB3 interval are shown in Table 1 (SEQ.ID.NOS.:5-20). 112 sporadic patients were genotyped to find patients who were carrying the same alleles as those identified in the families linked at the PDB3 locus (haplotypes: PDB3H1 and PDB3H2). The alleles of the markers tested defined a genetic signature that was used to further refine the PDB3 genetic interval within markers CA5-5 and CA5-26.

Construction of an Integrated Physical Map of the PDB3 Locus

Given a genetically defined interval by genetic and meiotic recombinants, a contig of genomic clones that spans the interval needs to be generated. Publicly available resources, such as The National Center for Bioinformatics, and the Laurence Livermore Laboratory (Chromosome 5 map of March 2001), provide aligned chromosome maps of genetic markers, sequence tagged sites (STSs), radiation hybrid map data, CEPH yeast artificial chromosome (YACs) clones, bacterial artificial chromosomes (BACs) and P1 artificial chromosomes (PACs). The inventors used some of these resources that are all available electronically to build in silico a BAC contig covering the PDB3 locus. Oligonucleotide primer pairs for the markers located in the interval were synthesized to validate some of the BACs that spanned the genetically defined interval.

Genomic Sequencing of Candidate Genes for Paget Disease of Bone within the Minimal Interval Resources from the Human Genome Project were used to identify in silico genes located within the genetic interval. These genes represent potential candidates for causing Paget disease of bone. These genes were map in silico on the BAC contig in the tiling path. Some expressed sequence tags (ESTs), were also map in silico on the BAC contig. Several genes of these candidate genes were sequenced but no mutations were found in them.

Mutation Screening of the p62/SQSTM1 Gene and Identification of a Mutation Causing Paget Disease of Bone Among the many genes that were screened for mutation, one of these genes was the atypical protein kinase C-interacting protein p62/sequestosome 1 (p62/SQSTM1). Table 2 shows the sequence of the primers used to sequence the p62/SQSTM1 gene (SEQ.ID.NOS.:21-36). One nucleotide variation at nucleotide position 1215 of the p62/SQSTM1 gene, changing amino acid Pro to Leu at amino acid position 392 (Pro392Leu), was detected in 11 kindreds of the family resources. This variation was found to be segregating with the disorder in these families. Sequencing the 112 sporadic cases revealed that 18 patients also carried the variation. Sequencing of 86 non-affected spouses and 205 individuals from the general population did not reveal any change in the wild-type p62/SQSTM1 sequence. These data therefore demonstrate that the C to T variation at position 1215 of the p62/SQSTM1 gene is, in fact, a mutation causing Paget disease of bone.

No additional disease-causing mutations were found. However, five SNPs were identified: 380C→T (A117V), in exon 3; 862G→C (Q274E), in exon 6; 916C→T (D292D), in exon 6; 976G→A (R312R), in exon 6; and 994C→A (S318S), in exon 6. Frequencies of these five SNPs were similar between affected and unaffected subjects. None of these SNPs had alleles associated with the mutation. However, two of these SNPs, 916C→T and 976G→A showed distinct alleles cosegregating with the disease haplotypes. For instance, the PDB3H1 haplotype harbored a T and an A at positions 916 and 976, respectively, whereas the PDB3H2 signature displayed a C and a G at these two positions.

TABLE 1

| Primers | Forward | | Reverse | |
|---|---|---|---|---|
| | Genotyping | | | |
| CA5-3 | ggagcaggattcaggaaggt | (SEQ.ID.NO.:5) | taccaagttctttcctgccc | (SEQ.ID.NO.:6) |
| CA5-5 | gtgtcatcattcccaggctt | (SEQ.ID.NO.:7) | agcattggcttagctcagga | (SEQ.ID.NO.:8) |
| CA5-6 | ctatctagcctgggcgacag | (SEQ.ID.NO.:9) | ttcctgtgatcttaacaccttcc | (SEQ.ID.NO.:10) |
| CA5-7 | aaggctcctccattccttgt | (SEQ.ID.NO.:11) | ccaccttcccgtctttaat | (SEQ.ID.NO.:12) |
| CA5-9 | gcctcaatggacataaacca | (SEQ.ID.NO.:13) | ggtgtcctatttcttcctgtatcaa | (SEQ.ID.NO.:14) |
| CA5-11 | actcacacacccaggcctac | (SEQ.ID.NO.:15) | caccatcagccagagactgt | (SEQ.ID.NO.:16) |
| CA5-25 | gggggtgtagagaggaaacc | (SEQ.ID.NO.:17) | aattggaatgccactcccta | (SEQ.ID.NO.:18) |
| CA5-27 | acgaccacgaaagtgacaca | (SEQ.ID.NO.:19) | cgcccggctaaaaatacat | (SEQ.ID.NO.:20) |

TABLE 2

| Primers | Sense | | Antisense | |
|---|---|---|---|---|
| | Sequencing | | | |
| p62/SQSTM1-1 | ggcccattttccgccagc | (SEQ.ID.NO.:21) | cttggtcaccactccagtca | (SEQ.ID.NO.:22) |
| p62/SQSTM1-2 | aggggtagtcttgcctctc | (SEQ.ID.NO.:23) | acagccctcaaattgctgac | (SEQ.ID.NO.:24) |
| p63/SQSTM1-3 | agtttcctggtggacccatt | (SEQ.ID.NO.:25) | gtgacagcccacagtgac | (SEQ.ID.NO.:26) |
| p62/SQSTM1-4 | ctgaattcttgccttgcaca | (SEQ.ID.NO.:27) | gcacctgtctgaggtgagc | (SEQ.ID.NO.:28) |
| p62/SQSTM1-5 | cccgtggtccagcactacta | (SEQ.ID.NO.:29) | agagtgggaggaaggagagg | (SEQ.ID.NO.:30) |
| p62/SQSTM1-6 | cttagctgcttgtggggact | (SEQ.ID.NO.:31) | ctccctcgggtttgtaagtg | (SEQ.ID.NO.:32) |
| p62/SQSTM1-7 | agaccctgcagccttaact | (SEQ.ID.NO.:33) | ccaactcctaacctcccaca | (SEQ.ID.NO.:34) |
| p62/SQSTM1-8 | cactgtggcctgtgaggac | (SEQ.ID.NO.:35) | cagtgagccttgggtctcg | (SEQ.ID.NO.:36) |

FULL CITATIONS FOR REFERENCES REFERRED TO IN THE SPECIFICATION

Barker D J, Chamberlain A T, Guyer P B, Gardner M J (1980) Paget's disease of bone: the Lancashire focus. Br Med J 280:1105-1107.

Barker D J (1984) The epidemiology of Paget's disease of bone. Br Med Bull 40:396-400.

Breanndan Moore S, Hoffman D L (1988) Absence of HLA linkage in a family with osteitis deformans (Paget's disease of bone). Tissue Antigens 31:69-70.

Cody J D, Singer F R, Roodman G D, Otterund B, Lewis T B, Leppert M, Leach R J (1997) Genetic linkage of Paget disease of the bone to chromosome 18q. Am J Hum Genet 61:1117-1122.

Darnay B G, Ni J, Moore P A, Aggarwal B B (1999) Activation of NF-kappaB by RANK requires tumor necrosis factor receptor-associated factor (TRAF) 6 and NF-kappaB-inducing kinase. Identification of a novel TRAF6 interaction motif. J Biol Chem 274:7724-7731.

Detheridge F M, Barker D J, Guyer P B (1983) Paget's disease of bone in Ireland. Br Med J (Clin Res Ed) 287: 1345-1346.

Fotino M, Haymovits A, Falk C T (1977) Evidence for linkage between HLA and Paget's disease. Transplant Proc 9:1867-1868.

Good D, Busfield F, Duffy D, Lovelock P K, Kesting J B, Cameron D P, Shaw J T (2001) Familial Paget's disease of bone: nonlinkage to the PDB1 and PDB2 loci on chromosomes 6p and 18q in a large pedigree. J Bone Miner Res 16:33-38.

Hamdy R C (1995) Clinical features and pharmacologic treatment of Paget's disease. Endocrinol Metab Clin North Am 24:421-436.

Haslam S I, Van Hul W, Morales-Piga A, Balemans W, San-Millan J L, Nakatsuka K, Willems P, Haites N E, Ralston S H (1998) Paget's disease of bone: evidence for a susceptibility locus on chromosome 18q and for genetic heterogeneity. J Bone Miner Res 13:911-917.

Hocking L, Slee F, Haslam S I, Cundy T, Nicholson G, van Hul W, Ralston S H (2000) Familial Paget's disease of bone: patterns of inheritance and frequency of linkage to chromosome 18q. Bone 26:577-580.

Hughes A E, Shearman A M, Weber J L, Barr R J, Wallace R G, Osterberg P H, Nevin N C, Mollan R A (1994) Genetic linkage of familial expansile osteolysis to chromosome 18q. Hum Mol Genet 3:359-361.

Kanis J A (1998) Pathophysiology and treatment of Paget's disease of bone. 2nd edition. In: Ltd Martin Dunitz (ed), London.

Klein R M, Norman A (1995) Diagnostic procedures for Paget's disease. Radiologic, pathologic, and laboratory testing. Endocrinol Metab Clin North Am 24:437-450.

Leach R J, Singer F R, Roodman G D (2001) The genetics of paget's disease of the bone. J Clin Endocrinol Metab 86:24-28.

Morales-Piga A A, Rey-Rey J S, Corres-Gonzalez J, Garcia-Sagredo J M, Lopez-Abente G (1995) Frequency and characteristics of familial aggregation of Paget's disease of bone. J Bone Miner Res 10:663-670.

Naito A, Azuma S, Tanaka S, Miyazaki T, Takaki S, Takatsu K, Nakao K, Nakamura K, Katsuki M, Yamamoto T, Inoue J (1999) Severe osteopetrosis, defective interleukin-1 signalling and lymph node organogenesis in TRAF6-deficient mice. Genes Cells 4:353-62.

Nance M A, Nuttall F Q, Econs M J, Lyles K W, Viles K D, Vance J M, Pericak-Vance M A, Speer M C (2000) Heterogeneity in Paget disease of the bone. Am J Med Genet 92:303-307.

Reasbeck J C, Goulding A, Campbell D R, Beale L R, Stewart R D (1983) Radiological prevalence of Paget's disease in Dunedin, New Zealand. Br Med J (Clin Res Ed) 286:1937.

Rosenbaum H D, Hanson D J (1969) Geographic variation in the prevalence of Paget's disease of bone. Radiology 92:959-963.

Guyer P B, Chamberlain A T (1980) Paget's disease of bone in two American cities. Br Med J 280:985.

Sanz L, Sanchez P, Lallena M J, Diaz-Meco M T, Moscat J (1999) The interaction of p62 with RIP links the atypical PKCs to NF-kappaB activation. Embo J 18:3044-53.

Sanz L, Diaz-Meco M T, Nakano H, Moscat J (2000) The atypical PKC-interacting protein p62 channels NF-kappaB activation by the IL-1-TRAF6 pathway. Embo J 19:1576-86.

Siris E S, Canfield R E (1990) Paget's disease of bone. In: K. L. B (ed) Principles and Practice of Endocrinology and Metabolism. J. B. Lippincott, Philadelphia, pp 504-512.

Siris E S, Ottman R, Flaster E, Kelsey J L (1991) Familial aggregation of Paget's disease of bone. J Bone Miner Res 6:495-500.

Sofaer J A, Holloway S M, Emery A E (1983) A family study of Paget's disease of bone. J Epidemiol Community Health 37:226-231.

Sparks A B, Peterson S N, Bell C, Loftus B J, Hocking L, Cahill D P, Frassica F J, Streeten E A, Levine M A, Fraser C M, Adams M D, Broder S, Venter J C, Kinzler K W, Vogelstein B, Ralston S H (2001) Mutation screening of the TNFRSF11A gene encoding receptor activator of NF kappa B (RANK) in familial and sporadic Paget's disease of bone and osteosarcoma. Calcif Tissue Int 68:151-155.

We claim:

1. A method of detecting Paget disease of bone in a human subject comprising: i) obtaining a sample from a human subject; ii) assaying the sample for a nucleic acid molecule encoding a mutated p62/SQSTM1 protein, wherein said nucleic acid molecule comprises the nucleic acid sequence of SEQ ID NO:3; and iii) determining that said human subject has Paget disease of bone if said nucleic acid molecule is present in the sample obtained from said human subject.

2. A method according to claim 1, wherein the assaying step comprises contacting the sample with a nucleotide probe capable of hybridizing with the nucleic acid molecule comprising the nucleic acid sequence of SEQ ID NO.:3 to form a hybridization product under conditions which permit formation of a hybridization product.

* * * * *

SEQUENCE LISTING

```
<160> NUMBER OF SEQ ID NOS: 36

<210> SEQ ID NO 1
<211> LENGTH: 2870
<212> TYPE: DNA
<213> ORGANISM: Homo sapiens

<400> SEQUENCE: 1
ggcctgggtg gcgaattcgg cacgaggctc gccgctcgct atggcgtcgc tcaccgtgaa      60
ggcctacctt ctgggcaagg aggacgcggc gcgcgagatt cgccgcttca gcttctgctg     120
```

```
cagccccgag cctgaggcgg aagccgaggc tgcggcgggt ccgggaccct gcgagcggct    180
gctgagccgg gtggccgccc tgttccccgc gctgcggcct ggcggcttcc aggcgcacta    240
ccgcgatgag gacggggact tggttgcctt ttccagtgac gaggaattga caatggccat    300
gtcctacgtg aaggatgaca tcttccgaat ctacattaaa gagaaaaaag agtgccggcg    360
ggaccaccgc ccaccgtgtg ctcaggaggc ccccgcaac atggtgcacc ccaatgtgat     420
ctgcgatggc tgcaatgggc tgtggtagg aacccgctac aagtgcagcg tctgcccaga     480
ctacgacttg tgtagcgtct gcgagggaaa gggcttgcac cggggggcaca ccaagctcgc   540 attccccagc cccttcgggc acctgtctga gggcttctcg cacagccgct ggctccggaa    600
ggtgaaacac ggacacttcg ggtggccagg atgggaaatg ggtccaccag gaaactggag    660
cccacgtcct cctcgtgcag gggaggcccg ccctggcccc acggcagaat cagcttctgg    720
tccatcggag gatccgagtg tgaatttcct gaagaacgtt ggggagagtg tggcagctgc    780
ccttagccct ctgggcattg aagttgatat cgatgtggag cacggaggga aagaagccg     840 cctgaccccc gtctctccag agagttccag cacagaggag aagagcagct cacagccaag    900
cagctgctgc tctgatccca gcaagccggg tgggaatgtt gagggcgcca cgcagtctct    960
ggcggagcag atgagaaaga tcgccttgga gtccgagggg cgccctgagg aacagatgga    1020
gtcggataac tgttcaggag gagatgatga ctggacccat ctgtcttcaa aagaagtgga   1080
cccgtctaca ggtgaactcc agtccctaca gatgccagaa tccgaagggc caagctctct   1140 ggaccctcc caggagggac ccacagggct gaaggaagct gccttgtacc cacatctccc    1200
gccagaggct gacccgcggc tgattgagtc cctctcccag atgctgtcca tgggcttctc   1260
tgatgaaggc ggctggctca ccaggctcct gcagaccaag aactatgaca tcggagcggc   1320
tctggacacc atccagtatt caaagcatcc cccgccgttg tgaccacttt gcccacctc    1380 ttctgcgtgc ccctcttctg tctcatagtt gtgttaagct tgcgtagaat tgcaggtctc   1440
tgtacaggcc agtttctctg ccttcttcca ggatcagggg ttagggtgca agaagccatt    1500
tagggcagca aaacaagtga catgaaggga gggtccctgt gtgtgtgtgt gtgctgatgt    1560
ttcctgggtg ccctggctcc ttgcagcagg gctgggcctg cgagacccaa ggctcactgc   1620
agcgcgctcc tgacccctcc ctgcaggggc tacgttagca gcccagcaca tagcttgcct   1680
aatggctttc actttctctt ttgttttaaa tgactcatag gtccctgaca tttagttgat   1740
tattttctgc tacagacctg gtacactctg attttagata aagtaagcct aggtgttgtc   1800
agcaggcagg ctggggaggc cagtgttgtg ggcttcctgc tgggactgag aaggctcacg   1860
aagggcatcc gcaatgttgg tttcactgag agctgcctcc tggtctcttc accactgtag   1920
ttctctcatt tccaaaccat cagctgcttt taaaataaga tctctttgta gccatcctgt    1980
taaatttgta aacaatctaa ttaaatggca tcagcacttt aaccaatgac gtttgcatag    2040
agagaaatga ttgacagtaa gtttattgtt aatggttctt acagagtatc tttaaaagtg   2100
ccttagggga accctgtccc tcctaacaag tgtatctcga ttaataacct gccagtccca   2160
gatcacacat catcatcgaa gtcttcccca gttataaaga ggtcacatag tcgtgtgggt   2220
cgaggattct gtgcctccag gaccaggggc ccacctctg cccagggagt ccttgcgtcc    2280
catgaggtct cccgcaagg cctctcagac ccagatgtga cggggtgtgt ggcccgagga    2340
agctggacag cggcagtggg cctgctgagg ccttctcttg aggcctgtgc tctggggtc     2400 ccttgcttag cctgtgctgg accagctggc ctggggtccc tctgaagaga ccttggctgc    2460
```

```
tcactgtcca catgtgaact tttctaggt ggcaggacaa atcgcgccca tttagaggat      2520
gtggctgtaa cctgctggat gggactccat agctccttcc caggacccct cagctccccg      2580
gcactgcagt ctgcagagtt ctcctggagg caggggctgc tgccttgttt caccttccat      2640
gtcaggccag cctgtccctg aaagagaaga tggccatgcc ctccatttgt aagaacaatg      2700
ccagggccca ggaggaccgc ctgccctgcc tgggccttgg ctgggcctct ggttctgaca      2760
ctttctgctg gaagctgtca ggctgggaca ggctttgatt ttgagggtta gcaagacaaa      2820
gcaaataaat gccttccacc tcaccgcaaa aaaaaaaaaa aaaaaaaaa                 2870

<210> SEQ ID NO 2
<211> LENGTH: 440
<212> TYPE: PRT
<213> ORGANISM: Homo sapiens

<400> SEQUENCE: 2
```

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Asp His Arg Pro Pro
            100                 105                 110

Cys Ala Gln Glu Ala Pro Arg Asn Met Val His Pro Asn Val Ile Cys
        115                 120                 125

Asp Gly Cys Asn Gly Pro Val Val Gly Thr Arg Tyr Lys Cys Ser Val
    130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
            180                 185                 190

Phe Gly Trp Pro Gly Trp Glu Met Gly Pro Pro Gly Asn Trp Ser Pro
        195                 200                 205

Arg Pro Pro Arg Ala Gly Glu Ala Arg Pro Gly Thr Ala Glu Ser
    210                 215                 220

Ala Ser Gly Pro Ser Glu Asp Pro Ser Val Asn Phe Leu Lys Asn Val
225                 230                 235                 240

Gly Glu Ser Val Ala Ala Ala Leu Ser Pro Leu Gly Ile Glu Val Asp
                245                 250                 255

Ile Asp Val Glu His Gly Gly Lys Arg Ser Arg Leu Thr Pro Val Ser
            260                 265                 270

Pro Glu Ser Ser Ser Thr Glu Glu Lys Ser Ser Ser Gln Pro Ser Ser
        275                 280                 285

Cys Cys Ser Asp Pro Ser Lys Pro Gly Gly Asn Val Glu Gly Ala Thr
    290                 295                 300

```
Gln Ser Leu Ala Glu Gln Met Arg Lys Ile Ala Leu Glu Ser Glu Gly
305                 310                 315                 320

Arg Pro Glu Glu Gln Met Glu Ser Asp Asn Cys Ser Gly Gly Asp Asp
            325                 330                 335

Asp Trp Thr His Leu Ser Ser Lys Glu Val Asp Pro Ser Thr Gly Glu
            340                 345                 350

Leu Gln Ser Leu Gln Met Pro Glu Ser Glu Gly Pro Ser Ser Leu Asp
            355                 360                 365

Pro Ser Gln Glu Gly Pro Thr Gly Leu Lys Glu Ala Ala Leu Tyr Pro
    370                 375                 380

His Leu Pro Pro Glu Ala Asp Pro Arg Leu Ile Glu Ser Leu Ser Gln
385                 390                 395                 400

Met Leu Ser Met Gly Phe Ser Asp Glu Gly Gly Trp Leu Thr Arg Leu
                405                 410                 415

Leu Gln Thr Lys Asn Tyr Asp Ile Gly Ala Ala Leu Asp Thr Ile Gln
            420                 425                 430

Tyr Ser Lys His Pro Pro Pro Leu
435                 440

<210> SEQ ID NO 3
<211> LENGTH: 2870
<212> TYPE: DNA
<213> ORGANISM: Homo sapiens

<400> SEQUENCE: 3
ggcctgggtg gcgaattcgg cacgaggctc gccgctcgct atggcgtcgc tcaccgtgaa      60
ggcctacctt ctgggcaagg aggacgcggc gcgcgagatt cgccgcttca gcttctgctg     120
cagccccgag cctgaggcgg aagccgaggc tgcggcgggt ccgggaccct gcgagcggct     180
gctgagccgg gtggccgccc tgttccccgc gctgcggcct ggcggcttcc aggcgcacta     240
ccgcgatgag gacgggggact tggttgcctt ttccagtgac gaggaattga caatggccat     300
gtcctacgtg aaggatgaca tcttccgaat ctacattaaa gagaaaaaag agtgccggcg     360
ggaccaccgc ccaccgtgtg ctcaggaggc ccccgcaac atggtgcacc ccaatgtgat     420
ctgcgatggc tgcaatgggc tgtggtagg aacccgctac aagtgcagcg tctgcccaga     480
ctacgacttg tgtagcgtct gcgagggaaa gggcttgcac cggggggcaca ccaagctcgc     540 attccccagc cccttcgggc acctgtctga gggcttctcg cacagccgct ggctccggaa     600
ggtgaaacac ggacacttcg gtggccagga tgggaaatg gtccaccag gaaactggag     660 cccacgtcct cctcgtgcag gggaggcccg ccctggcccc acggcagaat cagcttctgg     720
tccatcggag gatccgagtg tgaatttcct gaagaacgtt ggggagagtg tggcagctgc     780
ccttagccct ctgggcattg aagttgatat cgatgtggag cacggaggga aagaagccg     840 cctgaccccc gtctctccag agagttccag cacagaggag aagagcagct cacagccaag     900
cagctgctgc tctgatccca gcaagccggg tgggaatgtt gagggcgcca cgcagtctct     960
ggcggagcag atgagaaaga tcgccttgga gtccgagggg cgccctgagg aacagatgga    1020
gtcggataac tgttcaggag agatgatga ctggaccat ctgtcttcaa aagaagtgga    1080
cccgtctaca ggtgaactcc agtccctaca gatgccagaa tccgaaggc caagctctct    1140 ggacccctcc caggagggac ccacagggct gaaggaagct gccttgtacc cacatctccc    1200
gccagaggct gacctgcggc tgattgagtc cctctcccag atgctgtcca tgggcttctc    1260
tgatgaaggc ggctggctca ccaggctcct gcagaccaag aactatgaca tcggagcggc    1320
```

```
tctggacacc atccagtatt caaagcatcc cccgccgttg tgaccacttt tgcccacctc    1380
ttctgcgtgc ccctcttctg tctcatagtt gtgttaagct gcgtagaat tgcaggtctc     1440 tgtacaggcc agtttctctg ccttcttcca ggatcagggg ttagggtgca agaagccatt    1500
tagggcagca aaacaagtga catgaaggga gggtccctgt gtgtgtgtgt gtgctgatgt    1560 ttcctggggtg ccctggctcc ttgcagcagg gctgggcctg cgagaccaa ggctcactgc    1620 agcgcgctcc tgaccctcc ctgcaggggc tacgttagca gcccagcaca tagcttgcct     1680
aatggctttc actttctctt ttgttttaaa tgactcatag gtccctgaca tttagttgat    1740
tattttctgc tacagacctg gtacactctg attttagata aagtaagcct aggtgttgtc    1800
agcaggcagg ctggggaggc cagtgttgtg ggcttcctgc tgggactgag aaggctcacg    1860
aagggcatcc gcaatgttgg tttcactgag agctgcctcc tggtctcttc accactgtag    1920
ttctctcatt tccaaaccat cagctgcttt taaaataaga tctctttgta gccatcctgt    1980
taaatttgta aacaatctaa ttaaatggca tcagcacttt aaccaatgac gtttgcatag    2040
agagaaatga ttgacagtaa gtttattgtt aatggttctt acagagtatc tttaaaagtg    2100
ccttagggga accctgtccc tcctaacaag tgtatctcga ttaataacct gccagtccca    2160
gatcacacat catcatcgaa gtcttcccca gttataaaga ggtcacatag tcgtgtgggt    2220
cgaggattct gtgcctccag gaccaggggc ccaccctctg cccagggagt ccttgcgtcc    2280
catgaggtct tcccgcaagg cctctcagac ccagatgtga cggggtgtgt ggcccgagga    2340
agctggacag cggcagtggg cctgctgagg ccttctcttg aggcctgtgc tctggggtc     2400 ccttgcttag cctgtgctgg accagctggc ctggggtccc tctgaagaga ccttggctgc    2460
tcactgtcca catgtgaact ttttctaggt ggcaggacaa atcgcgccca tttagaggat    2520
gtggctgtaa cctgctggat gggactccat agctccttcc caggacccct cagctccccg    2580
gcactgcagt ctgcagagtt ctcctggagg caggggctgc tgccttgttt caccttccat    2640
gtcaggccag cctgtccctg aaagagaaga tggccatgcc ctccatttgt aagaacaatg    2700
ccagggccca ggaggaccgc ctgccctgcc tgggccttgg ctgggcctct ggttctgaca    2760
ctttctgctg gaagctgtca ggctgggaca ggctttgatt ttgagggtta gcaagacaaa    2820
gcaaataaat gccttccacc tcaccgcaaa aaaaaaaaaa aaaaaaaaa                 2870
```

<210> SEQ ID NO 4
<211> LENGTH: 440
<212> TYPE: PRT
<213> ORGANISM: Homo sapiens

<400> SEQUENCE: 4

```
Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Asp His Arg Pro Pro
```

-continued

```
              100                 105                 110
Cys Ala Gln Glu Ala Pro Arg Asn Met Val His Pro Asn Val Ile Cys
        115                 120                 125

Asp Gly Cys Asn Gly Pro Val Val Gly Thr Arg Tyr Lys Cys Ser Val
    130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
            180                 185                 190

Phe Gly Trp Pro Gly Trp Glu Met Gly Pro Pro Gly Asn Trp Ser Pro
        195                 200                 205

Arg Pro Pro Arg Ala Gly Glu Ala Arg Pro Gly Pro Thr Ala Glu Ser
    210                 215                 220

Ala Ser Gly Pro Ser Glu Asp Pro Ser Val Asn Phe Leu Lys Asn Val
225                 230                 235                 240

Gly Glu Ser Val Ala Ala Ala Leu Ser Pro Leu Gly Ile Glu Val Asp
                245                 250                 255

Ile Asp Val Glu His Gly Gly Lys Arg Ser Arg Leu Thr Pro Val Ser
            260                 265                 270

Pro Glu Ser Ser Ser Thr Glu Lys Ser Ser Gln Pro Ser Ser
        275                 280                 285

Cys Cys Ser Asp Pro Ser Lys Pro Gly Gly Asn Val Glu Gly Ala Thr
    290                 295                 300

Gln Ser Leu Ala Glu Gln Met Arg Lys Ile Ala Leu Glu Ser Glu Gly
305                 310                 315                 320

Arg Pro Glu Glu Gln Met Glu Ser Asp Asn Cys Ser Gly Gly Asp Asp
                325                 330                 335

Asp Trp Thr His Leu Ser Ser Lys Glu Val Asp Pro Ser Thr Gly Glu
            340                 345                 350

Leu Gln Ser Leu Gln Met Pro Glu Ser Glu Gly Pro Ser Ser Leu Asp
        355                 360                 365

Pro Ser Gln Glu Gly Pro Thr Gly Leu Lys Glu Ala Ala Leu Tyr Pro
    370                 375                 380

His Leu Pro Pro Glu Ala Asp Leu Arg Leu Ile Glu Ser Leu Ser Gln
385                 390                 395                 400

Met Leu Ser Met Gly Phe Ser Asp Glu Gly Gly Trp Leu Thr Arg Leu
                405                 410                 415

Leu Gln Thr Lys Asn Tyr Asp Ile Gly Ala Ala Leu Asp Thr Ile Gln
            420                 425                 430

Tyr Ser Lys His Pro Pro Leu
        435                 440
```

<210> SEQ ID NO 5
<211> LENGTH: 20
<212> TYPE: DNA
<213> ORGANISM: Artificial Sequence
<220> FEATURE:
<223> OTHER INFORMATION: CA5-3 forward primer

<400> SEQUENCE: 5
ggagcaggat tcaggaaggt                                        20

<210> SEQ ID NO 6

```
<211> LENGTH: 20
<212> TYPE: DNA
<213> ORGANISM: Artificial Sequence
<220> FEATURE:
<223> OTHER INFORMATION: CA5-3 reverse primer

<400> SEQUENCE: 6
taccaagttc tttcctgccc                                                   20

<210> SEQ ID NO 7
<211> LENGTH: 20
<212> TYPE: DNA
<213> ORGANISM: Artificial Sequence
<220> FEATURE:
<223> OTHER INFORMATION: CA5-5 forward primer

<400> SEQUENCE: 7
gtgtcatcat tcccaggctt                                                   20

<210> SEQ ID NO 8
<211> LENGTH: 20
<212> TYPE: DNA
<213> ORGANISM: Artificial Sequence
<220> FEATURE:
<223> OTHER INFORMATION: CA5-5 reverse primer

<400> SEQUENCE: 8
agcattggct tagctcagga                                                   20

<210> SEQ ID NO 9
<211> LENGTH: 20
<212> TYPE: DNA
<213> ORGANISM: Artificial Sequence
<220> FEATURE:
<223> OTHER INFORMATION: CA5-6 forward primer

<400> SEQUENCE: 9
ctatctagcc tgggcgacag                                                   20

<210> SEQ ID NO 10
<211> LENGTH: 23
<212> TYPE: DNA
<213> ORGANISM: Artificial Sequence
<220> FEATURE:
<223> OTHER INFORMATION: CA5-6 reverse primer

<400> SEQUENCE: 10
ttcctgtgat cttaacacct tcc                                               23

<210> SEQ ID NO 11
<211> LENGTH: 20
<212> TYPE: DNA
<213> ORGANISM: Artificial Sequence
<220> FEATURE:
<223> OTHER INFORMATION: CA5-7 forward  primer

<400> SEQUENCE: 11
aaggctcctc cattccttgt                                                   20

<210> SEQ ID NO 12
<211> LENGTH: 20
<212> TYPE: DNA
<213> ORGANISM: Artificial Sequence
<220> FEATURE:
<223> OTHER INFORMATION: CA5-7 reverse primer

<400> SEQUENCE: 12
```
ccaccttccc cgtctttaat                                                    20

<210> SEQ ID NO 13
<211> LENGTH: 20
<212> TYPE: DNA
<213> ORGANISM: Artificial Sequence
<220> FEATURE:
<223> OTHER INFORMATION: CA5-9 forward primer

<400> SEQUENCE: 13
gcctcaatgg acataaacca                                                    20

<210> SEQ ID NO 14
<211> LENGTH: 25
<212> TYPE: DNA
<213> ORGANISM: Artificial Sequence
<220> FEATURE:
<223> OTHER INFORMATION: CA5-9 reverse primer

<400> SEQUENCE: 14
ggtgtcctat ttcttcctgt atcaa                                              25

<210> SEQ ID NO 15
<211> LENGTH: 20
<212> TYPE: DNA
<213> ORGANISM: Artificial Sequence
<220> FEATURE:
<223> OTHER INFORMATION: CA5-11 forward primer

<400> SEQUENCE: 15
actcacacac ccaggcctac                                                    20

<210> SEQ ID NO 16
<211> LENGTH: 20
<212> TYPE: DNA
<213> ORGANISM: Artificial Sequence
<220> FEATURE:
<223> OTHER INFORMATION: CA5-11 reverse primer

<400> SEQUENCE: 16
caccatcagc cagagactgt                                                    20

<210> SEQ ID NO 17
<211> LENGTH: 20
<212> TYPE: DNA
<213> ORGANISM: Artificial Sequence
<220> FEATURE:
<223> OTHER INFORMATION: CA5-25 forward primer

<400> SEQUENCE: 17
gggggtgtag agaggaaacc                                                    20

<210> SEQ ID NO 18
<211> LENGTH: 20
<212> TYPE: DNA
<213> ORGANISM: Artificial Sequence
<220> FEATURE:
<223> OTHER INFORMATION: CA5-25 reverse primer

<400> SEQUENCE: 18
aattggaatg ccactcccta                                                    20

<210> SEQ ID NO 19
<211> LENGTH: 20
<212> TYPE: DNA

```
<213> ORGANISM: Artificial Sequence
<220> FEATURE:
<223> OTHER INFORMATION: CA5-27 forward primer

<400> SEQUENCE: 19
acgaccacga aagtgacaca                                                   20

<210> SEQ ID NO 20
<211> LENGTH: 19
<212> TYPE: DNA
<213> ORGANISM: Artificial Sequence
<220> FEATURE:
<223> OTHER INFORMATION: CA5-27 reverse primer

<400> SEQUENCE: 20
cgcccggcta aaatacat                                                     19

<210> SEQ ID NO 21
<211> LENGTH: 18
<212> TYPE: DNA
<213> ORGANISM: Artificial Sequence
<220> FEATURE:
<223> OTHER INFORMATION: p62-1 sense primer

<400> SEQUENCE: 21
ggcccatttt ccgccagc                                                     18

<210> SEQ ID NO 22
<211> LENGTH: 20
<212> TYPE: DNA
<213> ORGANISM: Artificial Sequence
<220> FEATURE:
<223> OTHER INFORMATION: p62-1 antisense primer

<400> SEQUENCE: 22
cttggtcacc actccagtca                                                   20

<210> SEQ ID NO 23
<211> LENGTH: 20
<212> TYPE: DNA
<213> ORGANISM: Artificial Sequence
<220> FEATURE:
<223> OTHER INFORMATION: p62-2 sense primer

<400> SEQUENCE: 23 aggggggtagt cttgcctctc                                                  20

<210> SEQ ID NO 24
<211> LENGTH: 20
<212> TYPE: DNA
<213> ORGANISM: Artificial Sequence
<220> FEATURE:
<223> OTHER INFORMATION: p62-2 antisense primer

<400> SEQUENCE: 24
acagccctca aattgctgac                                                   20

<210> SEQ ID NO 25
<211> LENGTH: 20
<212> TYPE: DNA
<213> ORGANISM: Artificial Sequence
<220> FEATURE:
<223> OTHER INFORMATION: p62-3 sense primer

<400> SEQUENCE: 25
agtttcctgg tggacccatt                                                   20
```

```
<210> SEQ ID NO 26
<211> LENGTH: 19
<212> TYPE: DNA
<213> ORGANISM: Artificial Sequence
<220> FEATURE:
<223> OTHER INFORMATION: p62-3 antisense primer

<400> SEQUENCE: 26
gtgacagccc cacagtgac                                                19

<210> SEQ ID NO 27
<211> LENGTH: 20
<212> TYPE: DNA
<213> ORGANISM: Artificial Sequence
<220> FEATURE:
<223> OTHER INFORMATION: p62-4 sense primer

<400> SEQUENCE: 27
ctgaattctt gccttgcaca                                               20

<210> SEQ ID NO 28
<211> LENGTH: 19
<212> TYPE: DNA
<213> ORGANISM: Artificial Sequence
<220> FEATURE:
<223> OTHER INFORMATION: p62-4 antisense primer

<400> SEQUENCE: 28
gcacctgtct gaggtgagc                                                19

<210> SEQ ID NO 29
<211> LENGTH: 20
<212> TYPE: DNA
<213> ORGANISM: Artificial Sequence
<220> FEATURE:
<223> OTHER INFORMATION: p62-5 sense primer

<400> SEQUENCE: 29
cccgtggtcc agcactacta                                               20

<210> SEQ ID NO 30
<211> LENGTH: 20
<212> TYPE: DNA
<213> ORGANISM: Artificial Sequence
<220> FEATURE:
<223> OTHER INFORMATION: p62-5 antisense primer

<400> SEQUENCE: 30
agagtgggag gaaggagagg                                               20

<210> SEQ ID NO 31
<211> LENGTH: 20
<212> TYPE: DNA
<213> ORGANISM: Artificial Sequence
<220> FEATURE:
<223> OTHER INFORMATION: p62-6 sense primer

<400> SEQUENCE: 31
cttagctgct tgtggggact                                               20

<210> SEQ ID NO 32
<211> LENGTH: 20
<212> TYPE: DNA
<213> ORGANISM: Artificial Sequence
<220> FEATURE:
```

```
<223> OTHER INFORMATION: p62-6 antisense primer

<400> SEQUENCE: 32
ctccctcggg tttgtaagtg                                               20

<210> SEQ ID NO 33
<211> LENGTH: 20
<212> TYPE: DNA
<213> ORGANISM: Artificial Sequence
<220> FEATURE:
<223> OTHER INFORMATION: p62-7 sense primer

<400> SEQUENCE: 33
agacccctgc agccttaact                                               20

<210> SEQ ID NO 34
<211> LENGTH: 20
<212> TYPE: DNA
<213> ORGANISM: Artificial Sequence
<220> FEATURE:
<223> OTHER INFORMATION: p62-7 antisense primer

<400> SEQUENCE: 34
ccaactccta acctcccaca                                               20

<210> SEQ ID NO 35
<211> LENGTH: 19
<212> TYPE: DNA
<213> ORGANISM: Artificial Sequence
<220> FEATURE:
<223> OTHER INFORMATION: p62-8 sense primer

<400> SEQUENCE: 35
cactgtggcc tgtgaggac                                                19

<210> SEQ ID NO 36
<211> LENGTH: 19
<212> TYPE: DNA
<213> ORGANISM: Artificial Sequence
<220> FEATURE:
<223> OTHER INFORMATION: p62-8 antisense primer

<400> SEQUENCE: 36
cagtgagcct tgggtctcg                                                19
```